US006927049B2

(12) United States Patent
Rubinsky et al.

(10) Patent No.: US 6,927,049 B2
(45) Date of Patent: Aug. 9, 2005

(54) CELL VIABILITY DETECTION USING ELECTRICAL MEASUREMENTS

(75) Inventors: Boris Rubinsky, Albany, CA (US); Yong Huang, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 241 days.

(21) Appl. No.: 10/079,940

(22) Filed: Feb. 19, 2002

(65) Prior Publication Data

US 2002/0137121 A1 Sep. 26, 2002

Related U.S. Application Data

(63) Continuation-in-part of application No. 09/618,951, filed on Jul. 19, 2000, now Pat. No. 6,482,619, which is a continuation-in-part of application No. 09/358,510, filed on Jul. 21, 1999, now Pat. No. 6,300,108.

(51) Int. Cl.[7] .............................................. C12N 13/00
(52) U.S. Cl. ................................................... 435/173.7
(58) Field of Search ...................................... 435/173.7

(56) References Cited

U.S. PATENT DOCUMENTS

| | | | |
|---|---|---|---|
| 4,810,963 A | * 3/1989 | Blake-Coleman et al. .. | 324/204 |
| 5,098,843 A | 3/1992 | Calvin | |
| 5,134,070 A | 7/1992 | Casnig | |
| 5,173,158 A | 12/1992 | Schmukler | |
| 5,283,194 A | 2/1994 | Schmukler | |
| 5,991,697 A | 11/1999 | Nelson et al. | |
| 6,300,108 B1 | * 10/2001 | Rubinsky et al. ......... | 435/173.6 |
| 6,387,671 B1 | * 5/2002 | Rubinsky et al. ......... | 435/173.7 |
| 6,403,348 B1 | * 6/2002 | Rubinsky et al. ......... | 435/173.7 |
| 6,482,619 B1 | * 11/2002 | Rubinsky et al. ......... | 435/173.7 |
| 6,562,604 B2 | * 5/2003 | Rubinsky et al. ......... | 435/173.6 |
| 6,613,211 B1 | 9/2003 | McCormick et al. | |

OTHER PUBLICATIONS

Andreason, G.L., *J. Tiss. Cult. Meth.*, 15:56–62 (1993).
Barber, *Advances in Biomedical Engineering*, J.E.W. W. Beneken and V. Thevenin (eds) IOS Press pp. 165–173 (1993).
Cook et al., *IEEE Transactions on Biomedical Engineering*, 41(6):713–722 (Aug. 1994).
Duraiswami et al., *Engineering and Analysis with Boundary Elements*, 22:13–31 (1998).
Duraiswami et al., *Chemical Engineering Science*, 32(13):2185–2196 (1997).
Duraiswami et al., *Bounary Element Technology XII*, pp. 226–237 (1997).
Fox et al., Sampling Conductivity Images Via MCMC, Mathematics Department, Auckland University, New Zealand (May 1997).
Gencer et al., *IEEE Transactions on Biomedical Engineering*, 43(2):139–149 (Feb. 1996).
Gilbert et al., *Biochimica et Biophysica Act*, 1334:9–14 (1997).
Griffiths et al., *Phys. Med. Biol.*, 3(10):1465–1476 (Oct. 1989).
Griffiths et al., *IEEE Transactions on Biomedical Engineering*, 42:948–954 (1995).
Griffiths et al., *Phys. Med. Biol.*, 32(11):1435–1444 (1987).
Glidewell et al., *Biomed Sci Instrum*, 29:251–257 (1993).
Gumerov et al., *13th International Conference on Boundary Element Technology, BETECH*, Las Vegas, Nevada (Jun. 1999).
Hapala, I., *Critical Reviews in Biotechnology*, 17:105–122 (1997).
Heller et al., *Advanced Drug Delivery Reviews*, 35:119–129 (1999).
Ho et al., *Critical Reviews in Biotechnology*, 16:349–362 (1996).
Holder et al., *Proceedings of the X. International Conference on Electrical Bioimpedance*, pp. 479–482 (1997).
Hughes et al., *Physiol. Meas.*, 15: A199–A209 (1994).
Jaroszeski et al., *Advanced Drug Delivery Reviews*, 35:131–137 (1999).
Liu et al., *Clin. Phys. Physiol. Meas.*, 13(Suppl. A):197–200 (1992).
Lorquin, P.G., *Molecular Biotechnology*, 7:5–35 (1997).
Lundqvist et al., *Proc. Natl. Acad. Sci. USA*, 95:10356–10360 (1998).
Mir et al., *Cancerology*, 313(III):613–618 (1991).
Narayan et al., *J, Urol.*, 148:1600–1604 (1992).
Neumann et al., *EMBOJ*, 7:841–845 (1982).
Schmuckler, "Impedance Spectroscopy of biological cells," *Engineering in Medicine and Biology Society*, 1994. Engineering Advances: New Opportunities for Biomedical Engineers., Proceedings of the 16th Annual Internal Conference of the IEEE.
Sharma et al., *Biophysical Journal*, vol. 71:3229–3241 (1996).
Weaver, J.C., *Journal of Cellular Biochemistry*, 51:426–435 (1993).

* cited by examiner

*Primary Examiner*—Jean C. Witz
*Assistant Examiner*—Susan Hanley
(74) *Attorney, Agent, or Firm*—Karl Bozicevic; Bozicevic, Field & Francis LLP

(57) ABSTRACT

A method of determining information about cell viability and other characteristics relating to cell membrane permeability is disclosed. The method involves determining the effect of a cell on current flow and relating that effect to a known standard which standard may be a known healthy cell and thereby deducing the viability of the cell being tested. The cells being tested can be subjected to different environmental conditions such as surrounding chemicals, temperature, pH and pressure to determine the effects of such conditions on cell viability and/or cell permeability. The cell being tested can be in a cell suspension, grown on s ubstarte, in tissue in vitro or in tissue in vivo. The method provides substantially instantaneous results and need not include the use of dyes or other markers.

19 Claims, 16 Drawing Sheets

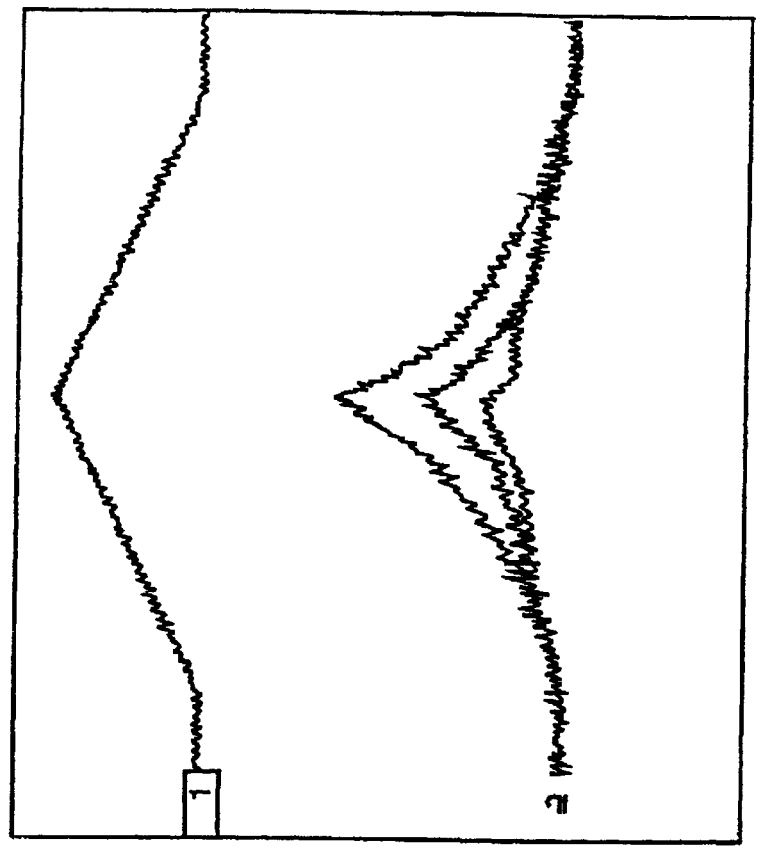
FIG. 8b REVERSIBLE
1) Ch 1: 20 Volt 100ms
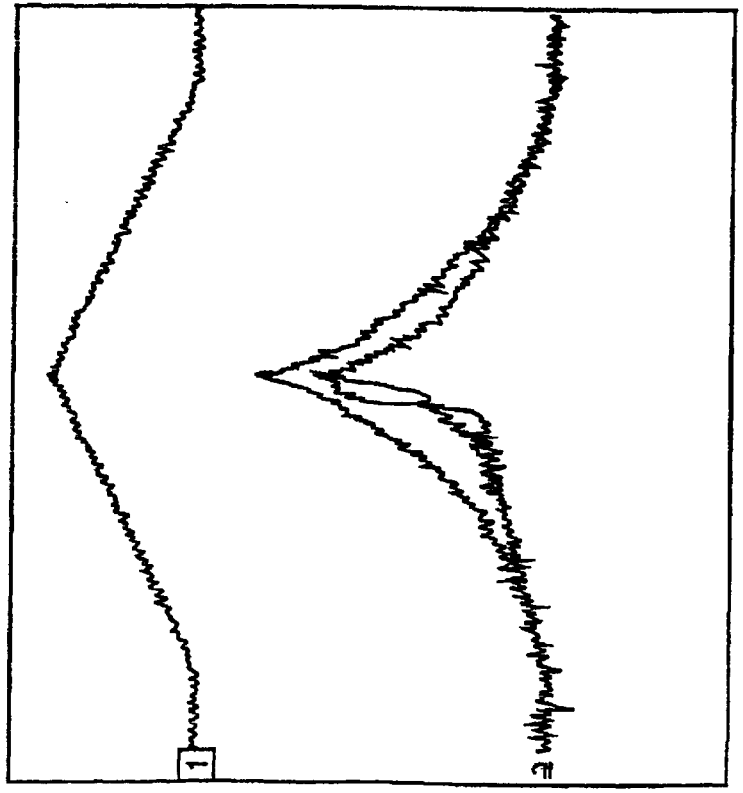
FIG. 8a IRREVERSIBLE
1) Ch 1: 20 Volt 100ms

CELL VIABILITY DETECTION USING ELECTRICAL MEASUREMENTS

CROSS-REFERENCES

This application is a continuation-in-part of application Ser. No. 09/618,951 which was filed Jul. 19, 2000 now U.S. Pat. No. 6,482,619 which is a continuation-in-part of application Ser. No. 09/358,510 filed Jul. 21, 1999 now U.S. Pat. No. 6,300,108 to which is claimed priority under 35 USC § 120 and which applications are incorporated herein by reference in their entirety.

FIELD OF THE INVENTION

This invention relates to the field of cell viability detection.

BACKGROUND OF THE INVENTION

In biological studies, it is important to distinguish between live and dead cells. This is important for situations in which cells: are in cellular suspensions, are grown on a substrate, are in tissue that is removed from the body or are in tissue in the body. For instance it is important to know prior to the study of a certain manipulation of the cells outside or inside the body if they are alive or not. This manipulation can be of different types such as: mechanical or electrical or chemical. For instance, when a drug or a chemical is tested on cells in suspension, or on substrates or in tissue it is important to know if the cells were alive prior to the test. Otherwise it is impossible to determine the effect of the drug or the chemical. Many times after the manipulation it is important to know if the cells are alive or not. For instance after chemical drug treatment of cancer it is important to know if the drug has killed the cells or not. Or for instance after a mechanical injury it is important to know if the traumatized cells are alive or not. Or for instance after thermal treatment of cancer with such methods as focused ultrasound, hyperthermia, electroporation or cryosurgery it is important to know if the treated cells are alive or not. In regular accidents it is important to know if the cells are alive for instance after the body was exposed to hypothermia or hypoxia. Or, after a stroke it is important to know what is the extent of tissue damage in the brain.

There are essentially two ways in which the viability of the cell can be determined. One is through their function and the other through their properties. An example of how to test viability through their function is by measuring their metabolism. For instance their ability to process glucose is used with positron emission tomography (PET) measurements. One of the most common methods to determine cell viability through their properties is by determination of the cell membrane integrity. The cell membrane has evolved to separate between the intracellular milieu and the extracellular. The function of the cell membrane is to maintain an intracellular environment compatible with the optimal function of the intracellular components and not to allow undesirable chemical to enter the cell interior. One of the main features separating dead from live cells is the loss of the physical integrity of the plasma membrane (Darzynkiewicz, Z., Li, X., and Gong, J. P. (1994) in Methods in Cell Biology Academic Press, Inc., New York; King, M. A. (2000) *J. Immunol. Methods* 243, 3–12.) When the membrane integrity is lost, chemicals that would otherwise not enter the cell can enter. Therefore, a variety of viability tests have been designed which test if chemical that cannot penetrate the membrane of intact cells, are inside the cells. The most common such chemicals are colorimetric dyes such as trypan blue and fluorescent dyes such as propidium iodide or YOYO-1 (Molecular Probes OR), which change the cell color once inside the cell (Horan, P. K., and Kapler, J. W. (1977) *J. Immunol Methods* 18, 309–316; Shapiro, H. M. (1995) in Practical Flow Cytometry Wiley, New York; Haugland, R. P. (1996) Handbook of Fluorescent Probes and Research Chemicals, Molecular Probes, Inc.) These chemicals are commonly used to determine cell viability in cells in suspension (Rui, J., Tatsutani, K. N., Dahiya, R., Rubinsky, B. Effect of thermal variables on human breast cancer in cryosurgery. *Breast Cancer Research and Treatment*, 53 182–192, 1999) as well as cells in tissue that was excised from the body (Pham, L., Rubinsky, B., "Breast tissue cryosurgery with antifreeze proteins" HTD-Vol. 362/BED-Vol. 40, Advances in Heat and Mass Transfer in Biotechnology—ASME Press, pp 171–175. 1998). However, the use of these colorimetric or fluorescent methods to detect cell viability through the measurement of the cell membrane integrity have certain drawbacks. First of all the methods require a first step that is the adding of a discrimination agents to the cell suspensions or to the tissue. Second, a certain period of time is needed for the cell to incorporate the discriminating chemical. Third, the presence of the discriminating chemical inside the cell must be determined through the use of cumbersome optical inspection apparatus, such as microscope or flow cytometry devices. These devices require direct interaction with the tested cells. Fourth, though widely used in biology and clinical research, the dye-exclusion based assays lack the capability to produce instantaneous and quantitative cell viability information, which is particularly important in the study of dynamics of cell death.

It is the purpose of the present invention to provide a cell viability assay that tests for the cell membrane integrity in a way that resolves drawbacks with the colorimetric or fluorescent dyes, listed above.

SUMMARY OF THE INVENTION

A method of testing of cell viability using electrical measurements of cell electrical properties is disclosed. The method comprises measuring the electrical properties of a cell or a plurality of cells in an electrically conductive medium. In one embodiment of the invention the cell is preferably placed in a opening in a material which blocks electrical current flow so that the electrical current can only flow from one electrode to another by essentially passing through the cell. After the cell is correctly positioned a voltage and a current are applied by creating an electrical potential difference between two electrodes. The current which flows from one electrode to another or current flowing from one point on one side of the cell to another point on another side of the cell and the relevant voltage are then detected. They are then compared to a standard such as a previous reading on a cell that has a known viability in order to determine the viability of the cell being tested. For example, the standard may be a standard of current flow of the same or similar type of cell which is known to be viable. If the current flow detected is the same or substantially the same then the cell being tested is also known to be viable. The standard may also be the voltage to current relation or the electrical impedance of the cell. The method can be repeated a plurality of times wherein one new cell after another is placed in the correct position so that electrical measurements can be applied, detected and then compared to a standard. Alternatively, a stream or flow of cells can be directed across an opening through which the current flows and is detected. It is also possible to include a plurality of cells which can be in the form of a piece of tissue in an opening surrounded by material which blocks electrical current flow in order to carry out the same process. The electrical current flow can be directed through different parts of the tissue in order to determine cell viability in different areas of the tissue.

In addition to the methodology for testing cells for viability the methodology disclosed here can be used in order to determine the effects, if any, of a compound or other changing environmental conditions may have on a cell. Thus, the method can be carried out in the same manner in which cell viability is tested by first testing the cell in a control environment and then adding a compound or changing a condition and again applying the same current to determine the effect of the new added compound or changed condition on the cell. Such a method is useful in testing chemicals or environmental changes to determine the effect of these changes or chemicals on the viability of a cell. The compound added may be a drug, a food additive or a chemical from the environment which is to be tested to determine if the drug or food additive or the chemical environment affect the viability of the cell being tested. The compound used in the test can be any compound and is not limited to drugs and food additives. For example, the compound could be any compound which might be expected to effect environmental conditions such as metals, metal salts, metal alloys and in particular heavy metals such as mercury. In a similar manner conditions such as temperature, pressure, pH and radiation can be changed to so as to determine the effects of such on the viability of the cell. Any or all of the conditions can be changed individually or simultaneously. The radiation may be any type of radiation including electromagnetic radiation, light, UV light, infrared light, or any type of particle or wave radiation which might be expected to effect cell viability. It may be desirable to carry out such testing in accordance with normal procedures of using a control whereby a number of cells are tested and retested without changing conditions in order to determine the effect of the electrical current on the cell in the absence of changing conditions. Thereafter, the control can be used to compare the results with an actual experiment where conditions such as an added compound are being added so that a clear understanding can be had that the actual conditions and not the applied electrical current is what is changing cell viability or the permeability of the cell membrane.

Devices, systems and particular methods are disclosed which make it possible to precisely monitor the movement of materials across a cell membrane. The information gained from monitoring the movement of materials across a cell membrane may be directly applied to deduce information with respect to the cell and/or its membrane. Alternatively, the information obtained from monitoring may be applied in order to control the movement of materials across the cell membrane such as by controlling the application of electrical current. Devices and systems of the invention make it possible to move charged molecules, and in particular ionic species, across a cell membrane and precisely monitor the occurrence of such. When carrying out electroporation using the devices, systems and methods of the invention the information obtained from monitoring the movement of the charged particles across the cell membrane is used to control the process of mass transfer across a cell membrane. Specifically, the system is used to obtain measurements and changes in electrical impedance across a cell membrane while the mass transfer properties of the cell are changed by the application of electrical current. Thus, information obtained on electrical impedance changes brought by the application of electrical current are used, in real time, in order to control the movement of charged molecules across a cell membrane.

One aspect of the invention is a method comprising creating an electrical charge differential between a first point and a second point separated from the first point by an electrically conductive medium comprising a biological cell. A first electrical parameter between the first and second points is then measured. A second electrical parameter is then adjusted based on the measuring of the first electrical parameter. The first electrical parameter may be any parameter such as one selected of the group consisting of current, voltage and electrical impedance. The second electrical parameter may be any parameter (the same as or different from the first electrical parameter) such as one selected from the group consisting of current, voltage or a combination of current and voltage.

In a preferred embodiment the method further includes placing a material in the electrically conductive medium, and adjusting the second electrical parameter in order to move the material into the biological cell. The material placed within the electrically conducted medium may be any material such as a pharmaceutically active compound or drug, a nucleotide sequence, a fluorescent dye, or a crystal which is specifically designed to effect the cell in a desired manner. In accordance with the method various conditions are adjusted so that the electrical potential between the two points is sufficiently high so as to cause the cell to be permeabilized. However, the conditions between the two points are further adjusted so that electroporation is reversible and as such does not cause cell death unless that is a result specifically being sought.

In another aspect of the invention the electroporation is not carried out for the purpose of moving material into or out of a cell but rather to analyze the cell or group of cells and provide information or diagnosis of the tissue or individual which contains the tissue. In accordance with this method an electrical charge differential is created between a first point and a second point separated from the first point by an electrically conducted medium comprising a biological cell. A first electrical parameter is then measured between the first and second points. The measuring of the first electrical parameter is then analyzed in order to determine a character of the cell and in particular a characteristic of a membrane of the cell. The first electrical parameter may be any parameter and is preferably selected from the group consisting of current, voltage and electrical impedance. A second electrical parameter is preferably adjusted in a manner which effects the membrane of the cell or cells present in the medium and the second electrical parameter is any parameter but preferably selected from current, voltage or a combination of both.

Another aspect of the invention is the device which is preferably comprised of a first electrode, a second electrode, a source of electricity which may later be connected to the electrodes. The source of electricity (e.g. a battery) is optionally present when the device is sold. The device further includes a means for hindering the flow of electrical current between the first and second electrodes except for electrical current flow through a defined route. Further, the device includes a means for measuring an electrical parameter such as current, voltage or electrical impedance through the defined route and a means for adjusting the source of electricity based on the measured electrical parameter. The means for hindering electrical current flow is preferably comprised of a non-conductive material and defined route comprised of one or more openings each with a diameter less than that of a biological cell so that a cell can fit within the defined route and have a current flow through but preferably not around the cell.

The device and systems of the invention can be used within the method in order to move a wide range of materials into or out of the biological cell in order to obtain a desired result. The process can be carried out on an individual cell, a group of cells, cells within a cell culture or within a living organism, e.g. cells within invertebrates and vertebrates including mammals as well as in plants. When carrying out the process on a plurality of cells (e.g. a tissue) a process of imaging the tissue and adjusting electrical current in real time based on images may be used. An imaging technology which may be applied is electrical impedance tomography (EIT). This technology relies on differences in bioelectrical attributes within the body or an organism (e.g. a human) to produce an image. In the method of the invention EIT images can be used in the same manner as the measuring step is used when the process is carried out on a single biological cell. In essence, the EIT technology makes it possible to "see" the effect of increased electrical current flow resulting from electroporation thereby providing information which can be used to precisely adjust the flow of electrical current so that cell membranes are permeabilized while not permanently disrupted.

Another aspect of the invention is a method which comprises sending an electrical current between a first point and a second point separated by the first point by an electrically conductive medium comprising tissue. The tissue may be present within a living organism such as a vertebrate or invertebrate and specifically includes mammals and humans. After the current is sent an image of the tissue is created wherein the image is based on an electrical parameter such as the electrical impedance of the tissue. Using the image as a guide an electrical parameter is adjusted in order to obtain a desired degree of electroporation of biological cells in the tissue. Electroporation will change electrical impedance and that change can be visualized on the image created. The electrical parameter adjusted may be any parameter such as current, voltage or a combination of both. In a preferred embodiment a material is placed in the electrically conducted medium such as being injected into the tissue and the adjustment of the current is carried out, based on the image, in a manner so as to move the material into biological cells of the tissue. The image created is preferably an impedance image created from known current inputs and measured input voltage using a reconstruction algorithm. The impedance image may be created from a known voltage input, a measured current input, or combination of known voltage input and measured current input.

A device for carrying out this method is another aspect of the invention which device includes a means for creating an electrical current across an electrically conducted medium. The device further includes a means for analyzing a first electrical parameter of the electrically conductive medium in order to create an image and a means for adjusting a second electrical parameter based on the image to obtain a desired degree of electroporation of biological cells in the electrically conductive medium. The first electrical parameter is preferably electrical impedance and the second electrical parameter is preferably selected from the group consisting of current, voltage or a combination of both. The current is preferably created by a plurality of electrodes positioned about an area of tissue upon which the electroporation is to be carried out.

The onset and extent of electroporation in a biological cell can be correlated to changes in the electrical impedance (which term is used herein to mean the ratio of current to voltage) of the biological cell or of a conductive medium that includes the biological cell. An increase in the current-to-voltage ratio across a biological cell occurs when the cell membrane becomes permeable due to pore formation or because of cell damage or other modes of cell membrane poration. Likewise, a decrease in the current-to-voltage ratio through a flowing conductive fluid occurs when the fluid draws a biological cell into the region between the electrodes in a flow-through electric cell. Thus, by monitoring the impedance of the biological cell or of an electrolyte solution in which the cell is suspended, one can detect the point in time in which pore formation in the cell membrane occurs, as well as the relative degree of cell membrane permeability due to the pore formation. This information can then be used to establish that a given cell has in fact undergone electroporation, or to control the electroporation process by governing the selection of the electrical parameters of the process e.g. the voltage magnitude. This discovery is also useful in the simultaneous electroporation of multitudes of cells in a cell culture or in vertebrates, invertebrates or plants. Specific embodiments apply the invention to mammals including humans. The process provides a direct indication of the actual occurrence of electroporation and an indication of the degree of electroporation averaged over all the cells being subjected to the process. The discovery is likewise useful in the electroporation of biological tissue (masses of biological cells with contiguous membranes) for the same reasons.

The benefits of this process include a high level of control over the onset and degree of electroporation, together with a more detailed knowledge of the occurrence and degree of permeability created in particular individual cells or cell masses. When applied to individual cells or to a succession of individual cells, this process assures that the individual cells are indeed rendered permeable and are indeed transformed by the introduction of chemical species. The process also offers the ability to increase the efficiency of electroporation by avoiding variations in the electrical environment that would destroy some cells while having an insufficient effect on others.

The invention can be understood by describing a simple embodiment which involves the use of an electrical device or system in which a biological cell can be placed and that contains a barrier that directs the electric current flow and hence the ion flow through a flow path that passes through the biological cell while permitting substantially no electric current to bypass the biological cell. In some of these embodiments, the invention involves the use of an apparatus containing two liquid-retaining chambers separated by a barrier that is substantially impermeable to an electric current. The barrier contains an opening that is smaller than the biological cell such that the biological cell once lodged in the opening will plug or close the opening. To achieve electroporation, the biological cell is secured over the opening by mechanical, chemical and/or biochemical means, preferably in a reversible manner so that the biological cell can later be removed without damage to the biological cell. Once the biological cell is secured over the opening, a voltage is imposed between the two chambers and across the biological cell residing in the opening. The passage of current between the chambers is thus restricted to a path passing through the opening and hence through the biological cell. By monitoring the current-voltage relation in the electric cell, the onset of electroporation is detected and the degree of pore formation is controlled, to both assure that electroporation is occurring and to prevent excessive pore formation and cell death. The user is thus afforded a highly precise knowledge and control of the condition of and the flux across the biological cell membrane.

In another series of embodiments, this invention is useful in the diffusive transport of chemical species into or out of a biological cell. In these embodiments, the cell is again divided into two chambers separated by a barrier, and the biological cell is lodged across an opening in the barrier in such a manner that the passage of liquid around the cell from one chamber to the other is substantially prevented. A liquid solution of the species to be introduced into the biological cell is placed in one or both of the chambers. The concentration of the species in the solution differs from that in the cell (either higher or lower, depending on whether one seeks to introduce or remove the species from the cell), or the concentration in one chamber differs from that in the other chamber.

In preferred methods of applying this invention to diffusive transport, the solutions in the two chambers differ in concentration such that the driving force for the diffusive transport is between the two chambers themselves rather than between the chambers and the interior of the biological cell. Knowledge and controlled monitoring of the concentrations in each of the two chambers on a periodic or continuous basis as the diffusion proceeds, together with the precise knowledge of the dimensions of the opening, enables the user to precisely observe and control the rate and amount of the species that enters the cell. The diffusion time can be controlled by imposing stepwise changes in the concentrations in either or both of the chambers, thereby imposing or removing the concentration differential. An application of particular interest is the combination of this type of diffusive transport of a chemical species with controlled electroporation as described in the preceding paragraph.

In addition to being useful in connection with electroporation technology the present invention can provide valuable information relating to a cell or group of cells or tissue containing a group of cells by monitoring electrical impedance and thereby providing information regarding the integrity of a cell membrane. Specifically, measurements are carried out regarding the movement of charged particles across a cell membrane. These measurements are related to the amount of electrical current needed to carry out the diffusion across a cell membrane. The information obtained can be analyzed directly or compared to previous measurements of a same tissue or measurements carried out on diseased or normal tissue thereby providing an indication of the amount of change which has occurred in the tissue being measured (based on an earlier measurement of the same tissues) or the amount of variance between the tissue being measured and tissue with impaired cell membranes (e.g. diseased cells) or a normal cell or tissue. The method is carried out in a manner similar to that used for conducting electroporation. However, no material needs to be added to the medium surrounding the cells. The device is similar in that it is divided into two portions with a positive electrode on one side and a negative electrode on another side separated by a barrier with the cells being positioned along openings on the barrier in a manner which allows for the passage of charged particles through the cell and through the opening in the barrier from one electrode to another. The barrier hinders or completely eliminates the flow of charged particles except through the openings. The measurement of electrical impedance between the electrodes make it possible to distinguish between cells with an intact membrane and cells with impaired membranes. By more precisely carrying out the measurements it is possible to make determinations with respect to the integrity of a normal cell membrane relative to an impaired (e.g. diseased) cell membrane.

Each of the various embodiments of this invention may be used with two or more (i.e. a plurality of) biological cells simultaneously, or cell masses such as in tissue which may be in an animal or plant during the process. The apparatus described above can be adapted for use with two or more biological cells by arranging the barrier such that the current or diffusive transport will be restricted to a flow path that passes through all of the cells while preventing bypass around the cells. A further application of the concepts of this invention is the electroporation of biological cells suspended in a flowing liquid. Electrodes are placed in fixed positions in the flow channel, and a voltage is imposed between the electrodes while current passing between the electrodes is monitored. Biological cells entering the region between the electrodes will lower the current, the impedance serving as an indication of the presence of one or more cells in the region, and optionally also as a signal to initiate the application of a higher voltage sufficient to achieve electroporation.

A further application of the device, system and method of the invention is the electroporation of biological cells present within a tissue which tissue may be present within a living organism such as a mammal. Electrodes are placed in fixed positions within the tissue, and voltage is applied between the electrodes while current passing between the electrodes is monitored. Biological cells with intact membranes in the region between the electrodes will increase the electrical impedance. Accordingly, a measurement of the electrical impedance provides an indication of the presence of one or more cells in the region. Electroporation will decrease the measured amount of impedance. When the process is carried out on a tissue then the measurement of electrical impedance is a statistical average of the cells present between the electrodes.

Electroporation methodology of the invention can be carried out on tissue in a living organism using an imaging technology which makes it possible to determine when (and preferably to some extent the degree) cell membranes are transformed so as to allow the flow of electrical current through their membranes. The preferred imaging technology is electrical impedance tomography (EIT) which provides a changing image created from information on differences in bioelectrical attributes of the tissue being imaged. A typical EIT image is acquired by injecting electrical currents into the body and measuring the resulting voltages through an electrode array. An impedance image is then produced from the known current inputs and the measured voltage data using a reconstruction algorithm. EIT is particularly appropriate for the implementation of the invention in tissue because it actually maps electrical impedances. Therefore, the region of tissue that will undergo electroporation and in which, consequently, the equivalent electrical impedance of the cells will change will be imaged by EIT. The image is used to adjust the electrical parameters (e.g. flow of electrical current) in a manner which allows electroporation to occur without damaging cell membranes.

The assay deals with measuring the electrical properties of the cell. We recognized that the cell membrane is essentially impermeable to ions in the extracellular and extracellular solution. Therefore, when the cell membrane is damaged and becomes permeable to discriminating extracellular chemicals it should become also permeable to ions. A change in the permeability of the cell membrane to ions expresses itself as a change in the electrical properties of the membrane, e.g. electrical impedance of the membrane and therefore of the cell. Measuring the electrical properties of the cell membrane and of the cell can provide an instantaneous measure of cell membrane integrity and cell viability.

One advantage of the invention over the use of chemical or fluorescent tags is that the ions are naturally present in any biological media and do not have to be added.

Another advantage is that their presence and effect is instantaneous and does not require a period of incubation as with some other discriminating chemicals.

Yet another advantage is that measuring the change in electrical properties of the cells does not require cumbersome optical means and can be done at a distance from the cells.

Yet another advantage is that electrical properties measurements can produce an instantaneous measure of cell membrane integrity as well as a quantitative measure related to the magnitude of the cell membrane damage.

Yet another advantage of the invention is that cells can be observed during the assay process to obtain additional information.

Yet another aspect of the invention is that specific information relating to cell membrane permeability can be obtained using the methodology of the invention.

One aspect of the invention comprises placing a cell in an electrically conductive medium wherein the cell blocks an opening in a material which material blocks current flow. Voltage is then applied across the cell and electrical current is detected through the cell to obtain a first signal. Conditions surrounding the cell are then changed and voltages reapplied to the cell and electrical current is again detected to obtain a second signal. The first signal is compared to the second signal thereby determining the effects of the changed condition on the cell. The changed condition can comprise adding compounds to the electrically conductive medium. Further, materials such as biological substance can be added to the electrically conductive medium and such substances can include materials such as proteins, nucleotide sequences, bacteria, viruses, infectious prions, fungus, and polysaccharides. In essence, any material can be added which one might want to determine what effect that material might have on the cellular membrane.

Among the advantages that this invention offers relative to the prior art are the ability to treat cells individually and to adapt the treatment conditions to the needs of individual cells. In embodiments where voltage is applied, the monitoring of the impedance affords the user knowledge of the presence or absence of pores and shows the progress of the pore formation and whether irreversible pore formation that might lead to cell death has occurred.

An advantage of the barrier-and-opening apparatus is the high sensitivity of the signal to noise ratio by virtue of its restriction of the current to a current flow path passing through the opening.

A still further advantage is the ability of the apparatus and method to be integrated into an automated system whereby the condition of each cell is monitored by instrumentation and individual cells are lodged in the opening and then removed at times governed by the monitored conditions.

An aspect of the invention is a method of controlling electroporation of biological cells in real time by adjusting an electrical parameter (e.g. voltage and/or current) applied to a system based on real time measurements of changes in current detected.

A feature of the invention is that the general concepts can be applied to carry out electroporation on a cell, multiple cells, a tissue or areas of tissues in a living animal.

An advantage of the invention is that a precise amount of electroporation can be obtained and cell damage avoided by controlling any given electrical parameter (e.g. current and/or voltage) applied based on real time measurements of changes in current which relates to the amount of electroporation being obtained.

Another advantage of the invention is that it can be used to transfect cells with nucleotide sequences without the need for packaging the sequences in a viral vector for delivery, thereby avoiding the cellular specificities of such vectors.

Still other advantages are that the process can be carried out relatively quickly with a relatively low degree of technical expertise.

Yet another advantage is that the process can be used to transfect cells without generating an immune response.

Still another advantage is that the process is not limited by the size of the DNA (i.e. the length of the DNA sequences) and the amount of DNA brought into a cell can be controlled.

Another feature of the invention is that imaging technologies such as EIT can be used to detect changes in impedance in a volume of cells.

Another feature of the invention is that it can use EIT in order to map impedance of an area of tissue and thereby detect changes in cell impedance in a volume of cells to adjust any given electrical parameter (e.g. current flow and/or voltage) to obtain desired electroporation.

These and further features, advantages and objects of the invention will be better understood from the description that follows.

BRIEF DESCRIPTION OF THE DRAWINGS

FIG. 3b is a transverse cross section of the device shown in FIG. 3a.

FIG. 8a is an image of current flow through cells with irreversible electroporation and FIG. 8b is an image of current flow through cells with reversible electroporation.

DESCRIPTION OF THE INVENTION AND SPECIFIC EMBODIMENTS

Figure 1:
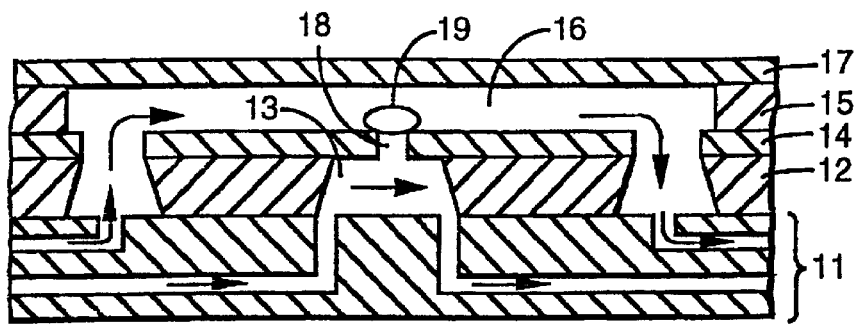
FIG. 1 is a cross section of a microdiffusion device useful in the practice of the present invention for infusing a biological cell with a chemical species without the assistance of an electrical current to effect electroporation.

Before the present devices and methods including methods for detecting cell viability are described, it is to be understood that this invention is not limited to particular methods and devices described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a biological cell" includes a plurality of such biological cells and reference to "an electrode" includes reference to one or more electrodes and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "electrode" is intended to mean any conductive material, preferably a metal, most preferably a non-corrosive metal that is used to establish the flow of electrical current from that electrode to another electrode. "Electrically conductive" means for transmitting electrical current that can be referred to in any manner, e.g. current or voltage. Electrodes are made of a variety of different electrically conductive materials and may be alloys or pure metals such as copper, gold, platinum, steel, silver, silver chloride, and alloys thereof. Further, the electrode may be comprised of a non-metal that is electrically conductive such as a silicon-based material used in connection with microcircuits. Typical electrodes used in tissue electroporation are preferably rod-shaped, flat plate-shaped or hollow needle-shaped structures. Electrodes may be used to deliver electrical current continuously or to deliver pulses. The electrodes may be very application-specific and be comprised of parallel stainless steel plates, implanted wires, needle pairs and needle arrays. Those skilled in the art will design specific electrodes that are particularly useful in connection with the desired results of obtaining electroporation in accordance with the present invention.

The term "tissue" shall mean a plurality of cells. The cells may be of the same or of a number of different types. These cells are preferably organized to carry out a specific function. Tissue includes tissue present within a living organism as well as removed tissue and may refer to in vivo or in vitro situations. Further, the tissue may be from any organism including plants and animals or a tissue developed using genetic engineering and thus be from an artificial source. In one embodiment the tissue is a plurality of cells present within a distinct area of a human.

The terms "device" and "electroporation device" are used interchangeably here for describing any a device as disclosed and described throughout. The device preferably includes a first electrode and a second electrode wherein the first and second electrodes are connected to a source of electricity in a manner so as to provide the electrodes with positive and negative charges respectively. The device also preferably includes a means for hindering the flow of electricity between the two electrodes except through one or more specific openings. For example the means for hindering flow can be a non-conductive material which has one or more openings therein wherein the openings are designed so as to specifically hold a biological cell or group of biological cells. Thereby the electrical current must flow through the opening and through the cells to the other electrode. The device also preferably includes a means for measuring the flow of electrical current between the electrodes. The means for measuring can include a volt meter, amp meter or any device known to those skilled in the art which is capable of measuring the flow of electrical current in any manner.

Further, the device preferably includes a means for adjusting the amount of electrical current flow between the electrodes. Thereby the voltage, current or other desired parameter of electrical current flow can be specifically adjusted based on the measured flow so as to obtain optimum electroporation of the cell or cells positioned between the electrodes. When the term "electroporation" is used it does not necessarily mean that the device is being used in order to move a compound such as a drug or DNA sequence into a cell.

The terms "power source", "source of electricity" and the like, are used interchangeably herein to describe any means for providing electrical power, current or voltage thereby creating a flow of electrical current between the electrodes. The device preferably is capable of providing for a controlled mode and amplitude and may provide constant DC current or AC current, provide pulse voltage or continuous voltage. Preferred devices are capable of exponentially decaying voltage, ramp voltage, ramped current, or any other combination. For example, a power supply may be used in combination with a chip of the type used in connection with microprocessors and provide for high-speed power amplification in connection with a conventional wall circuit providing alternating current at 110 volts. The pulse shape may be generated by a microprocessor device such as a Toshiba laptop running on a LabView program with output fed into a power amplifier. A wide range of different commercially-available power supplies can provide the desired function. The electrical potential delivered for electroporation is usually quoted in terms of the voltage gradients that develop in the affected region that is defined in units of V/cm developed in the tissue. Ranges include a range of 10 V/cm to 100,000 V/cm or more preferably 100 V/cm to 10,000 V/cm. However, the range is amplification-specific and can be extended outside the range for any desired application. Electrical pulses range from microseconds to milliseconds in general. However, other ranges of pulsing may be utilized depending on the desired results.

Invention in General

While this invention extends to a variety of structures, methods, and applications, this portion of the specification will illustrate certain specific structures and methods in detail, from which the concepts of the invention as a whole will become apparent.

A wide range of different devices and system can be used to carry out the method of the invention. The device must be comprised of a first electrode having a first voltage and a second electrode having a second voltage. Further, the device will comprise a means for detecting charged particle flow between electrodes and a means for varying the electrical current between electrodes based on data obtained by detecting changes in charged particle flow between electrodes. Preferably the device is further comprised of a component that prevents or substantially reduces charged particle flow between electrodes except for flow occurring through one or more biological cells positioned between the first and second electrodes.

Any desired material can be added to the medium in order to move that material into a cell which is present in the medium. Further, the invention does not necessarily include a process step of including a material into the medium which is to be brought into a cell. The process can be carried out merely to determine changes which occur in a cell membrane based on the electrical current applied. That information can be valuable to determine characteristics about the cell or group of cells present in the medium and, specifically, can be used to compare with information on normal and diseased cells or to determine the differences between previously tested cells and those currently being tested.

The first structure that will be discussed is an electroporation cell with an internal support to hold a single biological cell and an internal barrier that restricts the electric current flow in the electric cell to a flow path that passes through the biological cell. When no voltage is applied, the structure can be used for diffusive transport alone, unassisted by voltage-induced pore formation.

The configuration of the barrier, and the two chambers in embodiments that include two chambers, is not critical to the invention, and can vary widely while still serving the purposes and advantages of the invention. Since biological cells are microscopic in size, however, the preferred type of apparatus for the practice of this invention in each of its various forms is one in which the structure as a whole and/or its chambers are the size of electronic chips, fabricated by microfabrication techniques such as those used in electronic chip manufacture. It is further preferred that the chambers are constructed as flow-through chambers to allow the passage of the liquids in continuous flow, intermittent flow, or flow at the direction of the user, and to allow changes in the concentrations, pressure, and other conditions as needed to achieve close control over the passage of species across the biological cell membrane. Accordingly, a preferred structure and method of manufacture of the apparatus are those that involve the formation of the apparatus in layers or platelets with appropriate openings that form flow passages when the layers or platelets are bonded together.

Flow-through chambers offer the advantage of permitting the successive entry and removal of individual cells so that large numbers of cells can be treated in succession. Flow-through chambers also permit replenishment of solute-depleted solutions so that concentration gradients can be continuously maintained when desired. A further function that can be served by flow-through chambers is the increase and decrease of pressure, a function that is useful for various purposes as described below.

The support for the biological cell in this structure can be any structure that secures the biological cell in a fixed position and that allows the passage of electric current. The most convenient support is an opening in the barrier. Securement of a biological cell over the opening serves to close, seal or plug the opening, thereby directing the passage of electric current, diffusive transport, or both, through the cell and eliminating or minimizing leakage around the cell. A convenient mechanical means of achieving this is to impose a pressure differential across the opening in a direction that will press the cell against the opening. The diameter of the opening will be smaller than that of the cell, and the cell upon entering the apparatus will pass into one of the two chambers. By increasing the pressure in the chamber in which the cell resides, or lowering the pressure in the other chamber, the cell will be forced against the opening, closing it off. Once the procedure is completed, the cell is readily released from the opening by equalizing the pressures in the two chambers or by reversing the differential such that the higher pressure is in the chamber other than the chamber in which the cell was introduced. The flow of liquid in the chamber in which the cell was introduced will then remove the cell from the opening, exposing the opening for another cell.

An alternative method of sealing the opening with the cell is by the use of a coating on the barrier surface, or over the rim of the opening, of a substance that binds to the cell membrane. Since biological cell membranes are negatively charged, the coating may be a substance that bears a positive charge, such as polylysine, polyarginine, or polyhistidine. The biological cell can be directed to the opening by a pressure differential across the opening, and held in place by the coating. Once the procedure is completed, the cell can be released from the coating by momentarily increasing the flow rate of the liquid in the chamber on the cell side of the opening, or by imposing a reverse pressure differential across the opening to urge the cell away from the opening.

The size of the opening is not critical to the invention provided that the opening exposes sufficient surface area on the cell membrane to achieve the desired degree of either mass transfer, the passage of an electric current, or both, within a controllable and economically reasonable period of time. The optimal size will thus vary with the particular cells being treated or studied. In general, the opening is preferably circular or approximately circular in shape, and depending on the cell size, preferably ranges in diameter from about 1 micron to about 100 microns, more preferably from about 1 micron to about 50 microns, and most preferably from about 2 microns to about 20 microns. The barrier in which the hole is formed and which separates the two chambers is preferably of a rigid dielectric material that is impermeable to both water and solutes and that will hold a pressure differential sufficient to secure a cell against the opening. For devices that are manufactured by microfabrication techniques, a convenient material for the barrier is silicon nitride. Other materials that will serve equally well will be readily apparent to those skilled in the art.

A further feature of preferred embodiments of this invention is the use of apparatus made of transparent materials. This enables the user to observe cell interiors and the processes of microdiffusion and microelectroporation through a microscope as they occur.

Electroporation used in in Vivo Therapy

The electroporation techniques of the present invention are useful in connection with treating, analyzing or diagnosing an organism including mammals and humans in need of treatment. In general, treatment may be carried out by injecting a material continuously or in a rapid bolus into an area of tissue to be treated. Electrodes are placed adjacent to the tissue and current or voltage are applied and measured continuously in order to determine when the desired level of electroporation is obtained thereby making it possible to move the injected material into the cells of the tissue being treated.

The pharmaceutically active compound that is injected may be a conventional drug normally referred to as a small molecule or be a protein or nucleotide sequence that encodes a protein. Further, the composition injected into the tissue may be administered before, during or even after the application of electrical pulses from the electroporation device. The overall goal of the process is to provide for the opening of pores via electroporation and thereby introduce the compounds into the cells which compounds would not normally penetrate the cell membrane. For example, it is possible to introduce bleomicyn or various gene constructs and/or plasmids into cells of the tissue being treated. This is accomplished by generating electrical potentials and currents across the cells within the tissue to treated wherein the electrical potentials are generated as electrical pulses. It is preferable to utilize a plurality of electrodes as opposed to a single electrode in order to generate the pulses.

An example of a useful electrode design is one that is comprised of two flat steel strips 10 mm in width and 0.6 mm in thickness. The electrodes are spaced at a fixed distance of approximately 6 to 7 mm from each other. A second electrode design is comprised of two to as much as eight flat steel squares of 20 mm. The electrodes are connected to a PS15 electropulsator. Pulses can be delivered by placing the electrodes on the skin with the flat side on the skin or by placing the electrodes around skin tumors. Skin contact can be achieved by the use of materials conventionally used in connection with performing electrocardiographs such as electro-conductive gels or saline. In order to carry out the procedure a patient can receive one or a plurality of pulses and preferably receives a plurality of pulses. Different configurations can be designed in order to carry out electroporation of tissue inside an organism such as inside a human body, i.e. without applying electrodes outside the skin. Such configurations can be comprised of needle arrays that comprise a plurality of needle electrodes. As an example the positive and negative electrodes can each be comprised of six or more needles that are 0.5 mm in diameter and comprised of stainless steel, 1 cm in length connected to a BTX 820 pulse generator. The electrodes can be inserted in parallel into the tissue around the cells to be affected by electroporation. The electrodes can be positioned in circles of various diameters ranging from 5 mm to 1 cm. Voltage electrode ratio in the range of approximately 1300 V/cm can be used. Although any number of pulses can be delivered it is preferable to begin the process by delivering approximately six pulses in one second intervals with a pulse width of 100 microseconds. The present invention is particularly desirable in connection with electroporation of tissue in that the method can determine whether electroporation is occurring without the use of dyes and tags in order to track the material being brought inside the cell.

Figure 6A:
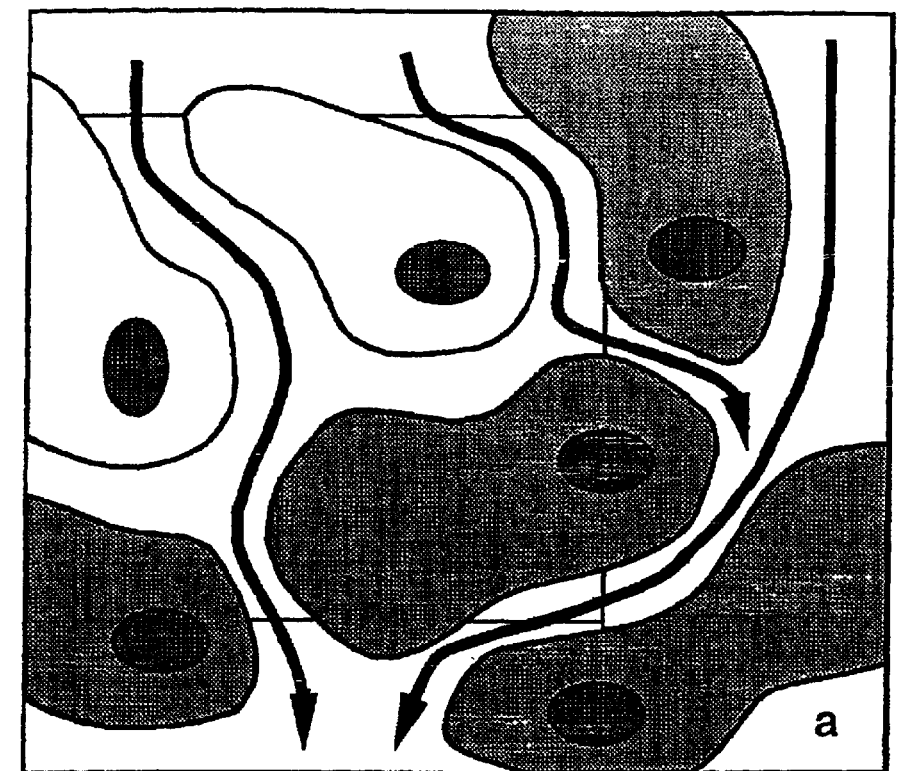
FIG. 6a shows current flow around cells prior to electroporation.
Figure 6B:
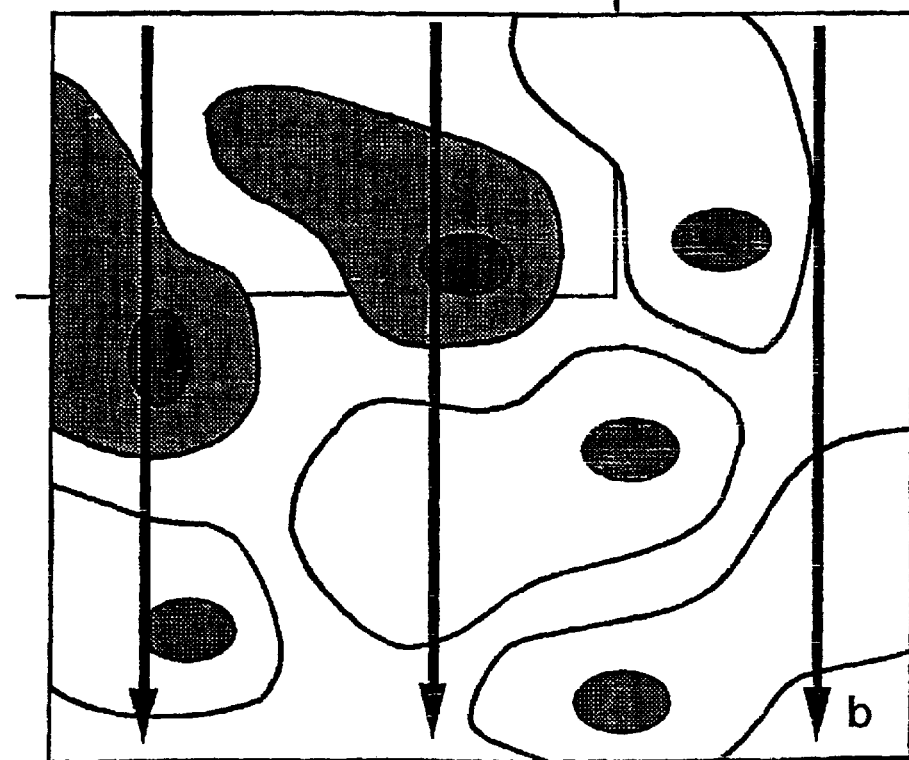
FIG. 6b shows electrical current flow through cells after (during) electroporation.

As shown in FIGS. 6a and 6b the electrical current can flow around the cells (FIG. 6a) or through the cells (FIG. 6b) after electroporation has taken place. The process of the invention makes it possible to determine the point when the transition is occurring between what is shown in FIG. 6a and what is occurring in FIG. 6b and further makes it possible to prevent the occurrence of irreversible effects on the cell membranes. As shown in FIG. 8a the electroporation can be carried out to such a great extent that cell membranes are damaged thereby resulting in irreversible effects on the cells. In general, this is undesirable. However, by modulating the amount of electrical current it is possible to obtain electroporation without significant damage to the cell membranes thereby obtaining a reversible situation as shown in FIG. 8b.

As shown in FIGS. 6a and 6b cells create electrical impedance and the present invention relates to precisely determining the degree of that electrical impedance and adjusting current so as to obtain desired results with respect to electroporation. However, when large numbers of cells are involved such as in a tissue it may be desirable to use other mechanisms for measuring other effects of the current in creating electroporation on a plurality of cells in the tissue. Electrical impedance is a measurement of how electricity travels through a given material. Every material has a different electrical impedance determined by it's electrical composition. Some materials have high electrical impedance and others have low electrical impedance. Breast tissue which is malignant (cancerous) has much lower electrical impedance (conducts electricity much better) than normal tissue or a benign (non-cancerous) tumor.

Impedance is a measurement of the degree to which an electrical circuit resists electrical-current flow when voltage is impressed across its terminals. Impedance expressed in OHMS, is the ratio of the voltage impressed across a pair of terminals to the current flow between those terminals. In direct-current (DC) circuits, impedance corresponds to resistance. In alternating current (AC) circuits, impedance is a function of resistance, inductance, and capacitance. Inductors and capacitors build up voltages that oppose the flow of current. This opposition is referred to as reactance, and must be combined with resistance to define the impedance. The resistance produced by inductance is proportional to the frequency of the alternating current, whereas the reactance produced by capacitance is inversely proportioned to the frequency.

The basic concepts described above are utilized in the basic aspects of the present invention and are also applicable to describing electrical impedance imaging also referred to as electrical impedance tomography (EIT). It should be noted that a number of different terminologies may be used to describe the same technique and those include applied potential tomography (APT). These imaging technologies make it possible to produce images based on the spatial variation of the electrical properties of the biological tissue. Techniques such as APT and EIT could be utilized to carry out the invention in connection with tissue. The applied potential tomography (APT) relies for its physical basis on the measurement of a potential distribution on a surface of a biological material, when an electrical current is applied between two points of its surface. Other researchers have utilized the technique and referred to it as electrical impedance imaging, conductivity imaging, electrical impedance tomography, etc. Herein, the technology is generally referred to as EIT or electrical impedance tomography. Accordingly, within the remainder of the disclosure the technology is referred to only as EIT technology and an example of such is shown within Example 3 below.

Those skilled in the art will contemplate different means of determining changes in electrical current upon reading this disclosure. A preferred method for determining such when carrying out the invention on tissue is to use imaging technology and specifically electrical impedance tomography (EIT) which monitors and analyzes differences in bioelectrical attributes of the sample being monitored in order to produce an image. The EIT technology can be used in connection with the present invention by creating an EIT image and using that image to adjust current flow to obtain desired results. Specifically, the EIT image is created by injecting electrical currents into the tissue and measuring the resulting voltages through an electrode array. This makes it possible to produce an impedance image from the known current inputs and the measured input voltage data using a reconstruction algorithm. The use of EIT technology is particularly desirable in connection with the present invention as applied to tissue in that EIT imaging provides a map of electrical impedances. The map of electrical impedances essentially allows the user to visualize when electroporation is beginning. When electroporation begins the user can stabilize the amount of current being applied and thereby avoid applying so much current as to result in irreversible damage to cells as shown in FIG. 8a. The EIT technology makes it possible for the region of tissue undergoing electroporation to be visualized based on changes in equivalent electrical impedance of the cells within tissue being monitored.

Figure 7:
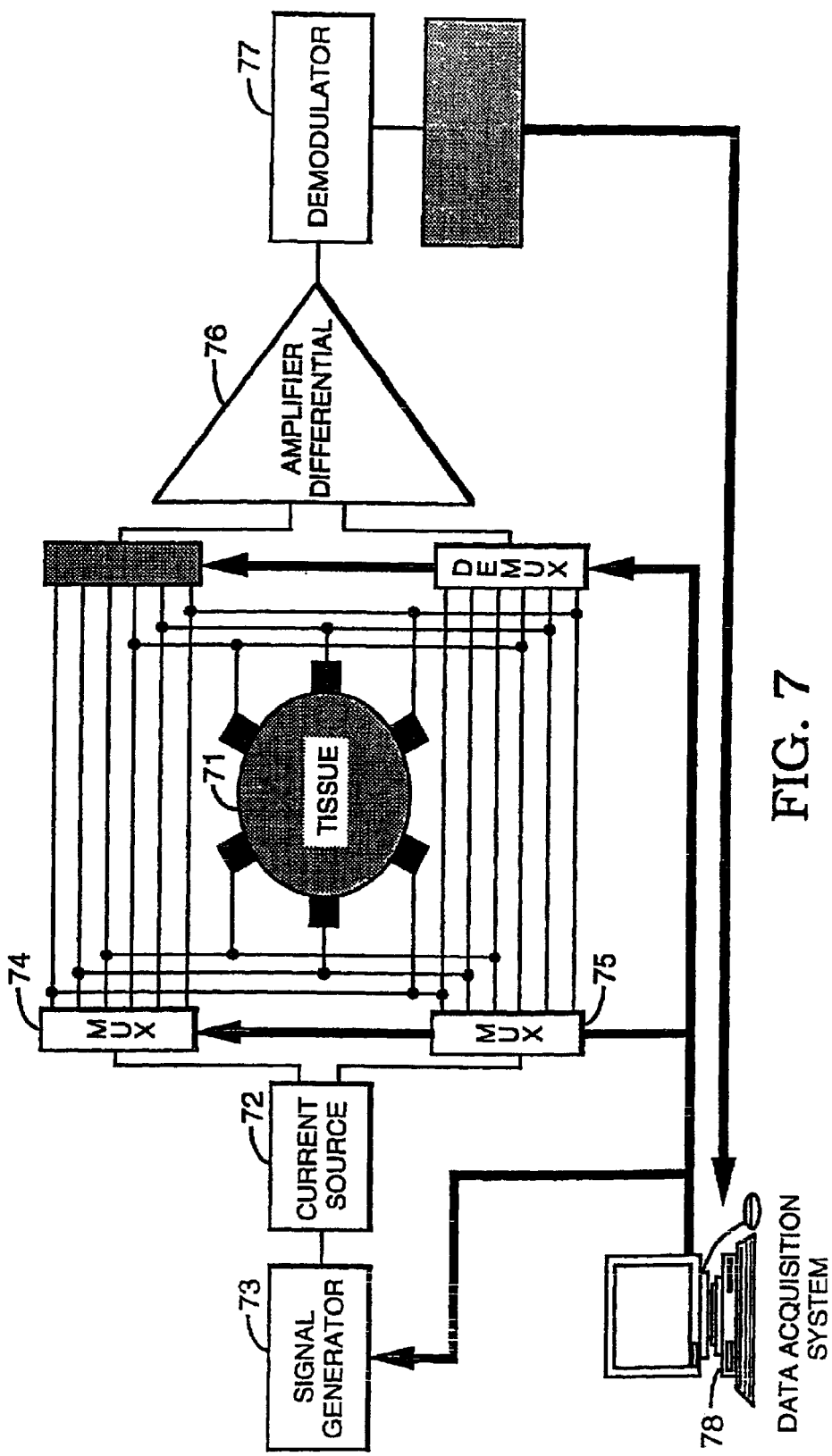
FIG. 7 shows a typical electrical impedance tomography (EIT) system for use with the invention.

FIG. 7 shows a conceptual view of an EIT system being used to carry out a process of the present invention on tissue 71. A current source 72 is controlled by a signal generator 73 and is used to drive an electrical current into the tissue sample 71 through a pair of computer controlled multiplexers 74 and 75 which lead to a differential amplifier 76 and demodulator 77. The measured signals are compared to the original in order to record amplitude and phase data for later image construction. The controlling computer 78 typically chooses which pair of electrodes will inject current while reading the remaining electrode voltages. There are a number of different hardware configurations which can be utilized in connection with the present invention.

The EIT system as shown in FIG. 7 is generally referred to as a serial system because of it's single current source and measurement amplifier. Varying degrees of parallelism (multiple current sources and voltage measuring amplifiers) have been utilized in other systems thereby increasing the flexibility and speed of the current injection system.

Reconstruction algorithms are used in order to take the voltage measured on an outer surface of a region of interest in the body (the injected current data) and information relating to the electrode geometry, and produce an image which represents spatial tissue impedance tissue distribution inside the region of the tissue 71. There are a number of methods which can be used to create an impedance image. Static imaging is the production of an absolute impedance distribution. Cook, R. D. et al. ACT3: a high speed, high precision electrical impedance tomography. IEEE, Trans. Biomed. Eng. 41, 713–22 (1994). Differential imaging methods produced distributions based on differences between two data sets. Barber, D. C. in Advances in Biomed Eng. (ed. Benek in, W., Thevenin, V.) 165–173 (IOS Press, Amsterdam, 1995). This type of technique provides an image of how the impedance distribution has changed from one baseline measurement. Multi frequency impedance imaging takes advantage of the frequency dependence of tissue impedance. Groffiths, H. The importance of phase measurement in electrical impedance tomography. Physics in Medicine and Biology 32, 1435–44 (1987). Quasi-static images can be produced using the above differential technique with a low frequency image used as the baseline. Accordingly the system makes it possible to produce a type of static imaging without the difficulties of true static imaging.

In order to provide for reconstruction and thus and image, a mathematical model of how the current behaves in the tissue is used. In general a model governing current flow in EIT is provided by the well-known Poisson equation. The type of mathematical analysis that is needed in EIT image reconstruction as well as many other medical imaging technologies, belongs to a general class known as boundary value problems. There are a number of different methods of solving boundary value problems. However, these problems can all be classified into either analytical or numerical iterative techniques and those skilled in the art can apply such in order to carry out the present invention.

The vast majority of reconstruction algorithms currently in use employ iterative numerical solutions to the Poisson equation. Most iterative numerical approaches attempt to solve the boundary value problem by guessing an impedance distribution in the tissue and repeatedly solving the forward problem (finding the voltage and current densities given an impedance distribution) and adjusting the impedance guesses correspondingly, until the voltage and currents measured fit those calculated. The forward problem must be solved numerically and is usually done so using finite element or finite difference schemes. The FEM is a very powerful and popular method of forward problem solution, and because of this, tends to dominate engineering solutions across many interdisciplinary fields.

An example of a microdiffusion apparatus in accordance with this invention for a single biological cell, for transporting materials across the cell membrane without the application of an electric field, is shown in FIG. 1. This components of this apparatus, from the bottom up, are an acrylic base 11, an intermediate silicon layer 12 (1 micron in thickness) with a portion 13 carved out to define the lateral boundaries of the lower of the two liquid chambers, a silicon nitride layer 14 serving as the barrier between the two chambers, a silicon washer 15 defining the lateral boundaries of the upper liquid chamber 16, and a glass cover plate 17. A hole 18 in the silicon nitride barrier serves as the opening, and a cell or contiguous cell mass such as tissue 19 is shown covering the hole. Channels extend through the acrylic base to serve as inlet and outlet channels for the liquids that pass through the upper and lower chambers, as shown by the arrows in the Figure.

When the pressure in the upper chamber 16 is higher than that in the lower chamber 13, the cell will be retained in position over the hole, serving as a plug separating the liquids in the two chambers from each other. When the composition of the solutions in the two chambers differs from that of the cell interior, mass transfer occurs across the cell membrane between the chambers and the cell. When the composition of the solution in one chamber differs from that in the other, mass transfer occurs through the cell from one chamber to the other. By precisely controlling the compositions of the solutions in the two chambers, one can precisely control the mass transfer rate and direction within the cell. Since the diameter of the opening 18 is known, one can precisely determine the mass transfer that occurs through the opening.

The numerous applications of this microdiffusion device will be readily apparent. For example, the device can be used to infuse a cell with a cryopreservative such as glycerol by filling the upper chamber 16 with physiological saline and the lower chamber 13 with glycerol. When using a cell 19 for which the mass transfer coefficient of glycerol across the cell membrane is known, one can readily calculate the amount of glycerol that will enter the cell and adjust the concentrations and exposure times to infuse the cell with the amount that is known to be required for cryopreservation.

Figure 2:
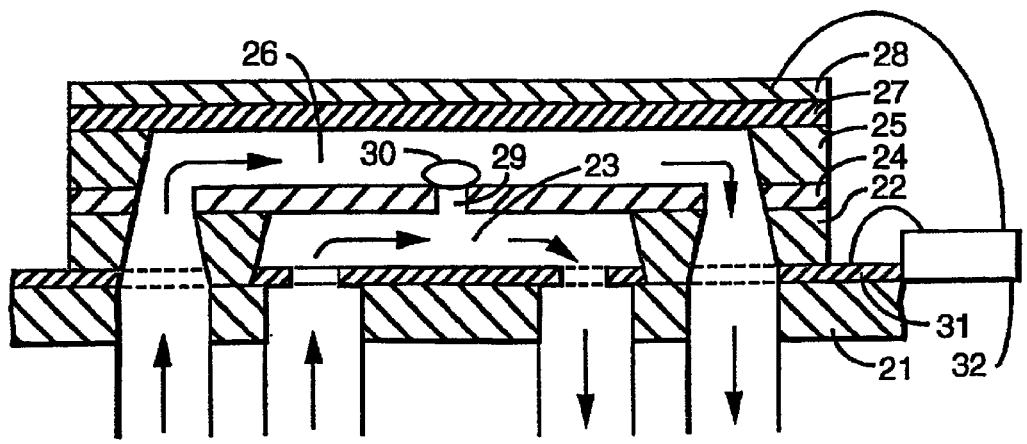
FIG. 2 is a cross section of a device useful in the practice of the present invention for achieving pore formation in a biological cell, and optionally for infusing the cell with a chemical species with the assistance of electroporation. This device is also generally useful for measuring electrical currents through cells to detect changes in membrane permeability due to changes in cell viability.

An example of a microelectroporation apparatus in accordance with this invention for a single biological cell, is shown in FIG. 2. The apparatus is similar in construction to the microdiffusion apparatus of FIG. 1. Its structural components, from the bottom up, are an acrylic base 21, a lower silicon layer 22 with a portion carved out to define the lateral boundaries of the lower liquid chamber 23, a silicon nitride layer 24 (1 micron in thickness) serving as the barrier between the two chambers, an upper silicon layer 25 defining the lateral boundaries of the upper liquid chamber 26, and a cover consisting of an n+poly-silicon layer (5,000 Å in thickness) 27 and a silicon nitride layer (1 micron in thickness) 28. A hole 29 in the silicon nitride barrier 24 serves as the opening, and a cell 30 (or cell mass) covers the hole. Channels extend through the acrylic base to serve as inlets and outlets for the liquids that pass through the upper and lower chambers, as shown by the arrows in the Figure. A further layer of n+poly-silicon (5,000 Å) 31 resides above the acrylic base 21, and this layer, together with n+ poly-silicon layer 27 above the upper chamber 26 serve as the two electrodes. Each electrode is joined by electric leads to a printed circuit board 32 which controls the voltage applied between the electrodes and measures the current passing between them.

The microelectroporation apparatus shown in FIG. 2 can be fabricated by conventional microfabrication techniques, typically involving chemical vapor deposition, masking, etching and sputtering. The operation of the apparatus will be analogous to the operation of the microdiffusion apparatus of FIG. 1. The movement of biological cells through the apparatus is achieved by suspending the cells in the liquid used to fill the upper chamber, and cells are drawn to the opening, one at a time, by imposing a pressure differential between the chambers, which also holds a cell in place once the cell has been drawn to the opening. A convenient method of imposing such a pressure differential is to maintain atmospheric pressure in the upper chamber while lowering the pressure in the lower chamber below atmospheric by attaching a syringe to the lower chamber and pulling on the syringe plunger. Care should be taken to limit the pressure differential to one that will not damage the cell.

Figure 3A:
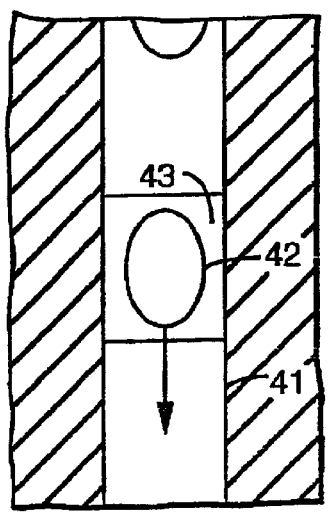
FIG. 3a is a longitudinal cross section of an electroporation device in accordance with this invention, designed for a mobile suspension of biological cells.
Figure 3B:
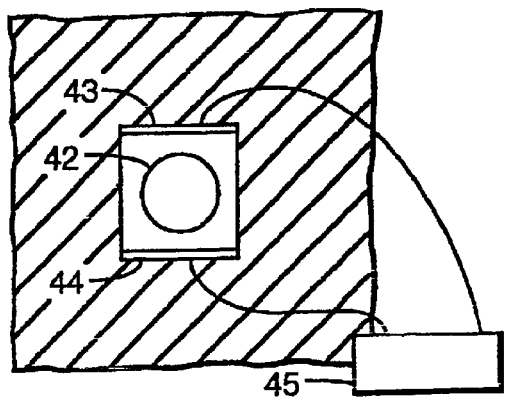

FIGS. 3a and 3b illustrate to a different apparatus and method within the scope of this invention. This apparatus and method involve a fluid suspension of biological cells flowing through a conduit or flow channel, in which the cells pass through a region between a pair of electrodes. The longitudinal cross section of FIG. 3a shows the walls 41 of the channel, and a biological cell 42 passing downward through the lumen of the channel (in the direction of the arrow). The transverse cross section of FIG. 3b shows that the channel is rectangular in cross section, although other cross-sectional geometries may be used. Electrodes 43, 44 are formed as coatings on two opposing walls of the channel. The electrodes are connected through leads to a printed circuit board 45 which measures the impedance and controls the voltage applied to the electrodes. The biological cell 42 is shown passing through the region between the two electrodes.

The area of the cross section of the channel is large enough to permit the cell to pass through essentially unimpeded by the channel walls, and yet small enough that only one cell can pass through the inter-electrode region at a time. In addition, each electrode 43, 44 is either approximately equal in length or slightly larger in length than the diameter of the biological cell, so that the cell upon entering the region causes a significant or measurable decrease in the current passing through the region due to the voltage applied across electrodes. The spacing of the electrodes, i.e., the distance between them, is likewise subject to the same considerations. The biological cells are suspended in a liquid solution of the species to be introduced into the cells, and the suspension is passed through the channel. A voltage is applied between the electrodes as suspension flows through the channel, and the current between the electrodes (or the impedance) is monitored. A significant drop in the current indicates the presence of a biological cell in the inter-electrode region. Once the cell is detected in this manner, an electroporation pulse can be applied to the electrodes while the cell is still in the inter-electrode region, and impedance can be observed further to detect the onset of electroporation. The species dissolved in the liquid solution will enter the cell as a result of the electroporation.

Variations on these structures and methods will be readily apparent to those skilled in the art. For example, the barriers described above can be minimized or avoided by using microelectrodes that are the same size as or smaller than the biological cells. Examples of such microelectrodes are carbon fiber microelectrodes (such as ProCFE, Axon Instruments, Foster City, Calif., USA) used in conjunction with high-graduation micromanipulators (such as those available from Narishige MWH-3, Tokyo, Japan). Microelectrodes can be used in place of the electrodes shown in FIG. 2 or in place of those shown in FIGS. 3a and 3b.

Figure 12:
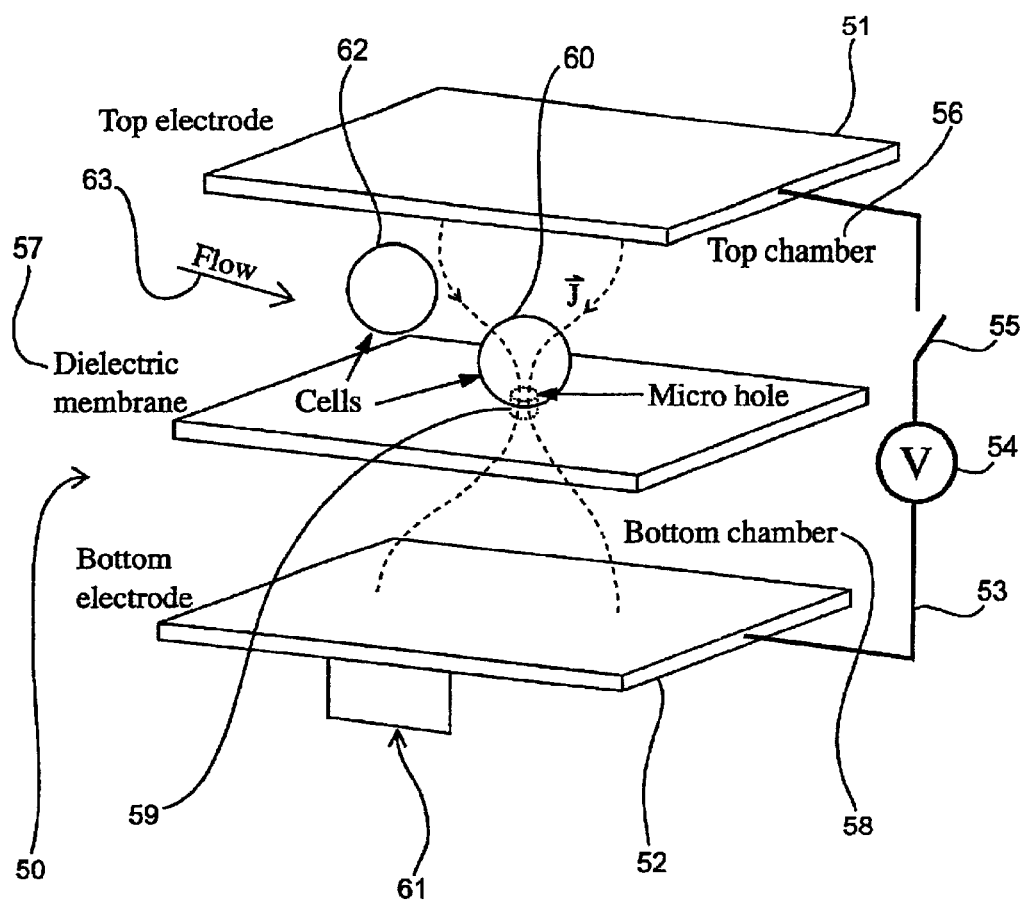
FIG. 12 is a perspective conceptual view of a cell viability detection device of the present invention.

FIG. 12 is a conceptual perspective view of an assay device 50 of the invention. The device 50 is comprised of a top electrode 51 and bottom electrode 52 with an electrical interconnection 53, electrical power source 54 and switch 55. A top chamber 56 includes an electrical conductive medium electrical can be any material such as water with ions therein. The top chamber 56 is bound on its top surface by the top electrode 51 and on its bottom surface by the dielectric membrane 57. The bottom chamber 58 is positioned above the bottom electrode 52 and below the dielectric membrane 57. In a manner similar to the top chamber 56 the bottom chamber 58 contains an electrically conductive medium e.g. DPES solution or saline solution.

The dielectric membrane 57 is comprised of a material which does not allow current to flow through from the top electrode to the bottom electrode. However the dielectric medium 57 includes a microhole 59. The microhole is preferably smaller in diameter than a single cell such as the cell 60 which is shown in place over the hole 59. When the switch 55 is closed completing the circuit an electrical potential is created between the top electrode 51 and the bottom electrode 52. Current can then flow from one electrode to another but due to the presence of the dielectric membrane 57 the current flow is limited to flow through the microhole 59. When the cell 60 is positioned over the hole 59 the current must flow through the cell 60. A current detection device, ampmeter or other means of measuring current such as the ampmeter device 61 can be placed on the electrode 52. Alternatively, the detection device or current detecting means of any sort 61 or sensor for such a device can be placed at other places where current might be detected.

After the current has been detected the level of current is compared to standard such as a standard taken against a known viable cell which is substantially the same as the cell being measured. If the current flow is substantially the same as the standard then the cell being tested is found to be viable. However, if the current flow is substantially greater than the standard then the tester can conclude that the cell being tested is not viable. After the cell 60 has been tested it can be replaced with another cell 62. It is possible to create a flow 63 of cells through the device so as to continually read one cell after another and instantaneously determine the viability of the cell being tested.

Figure 13:
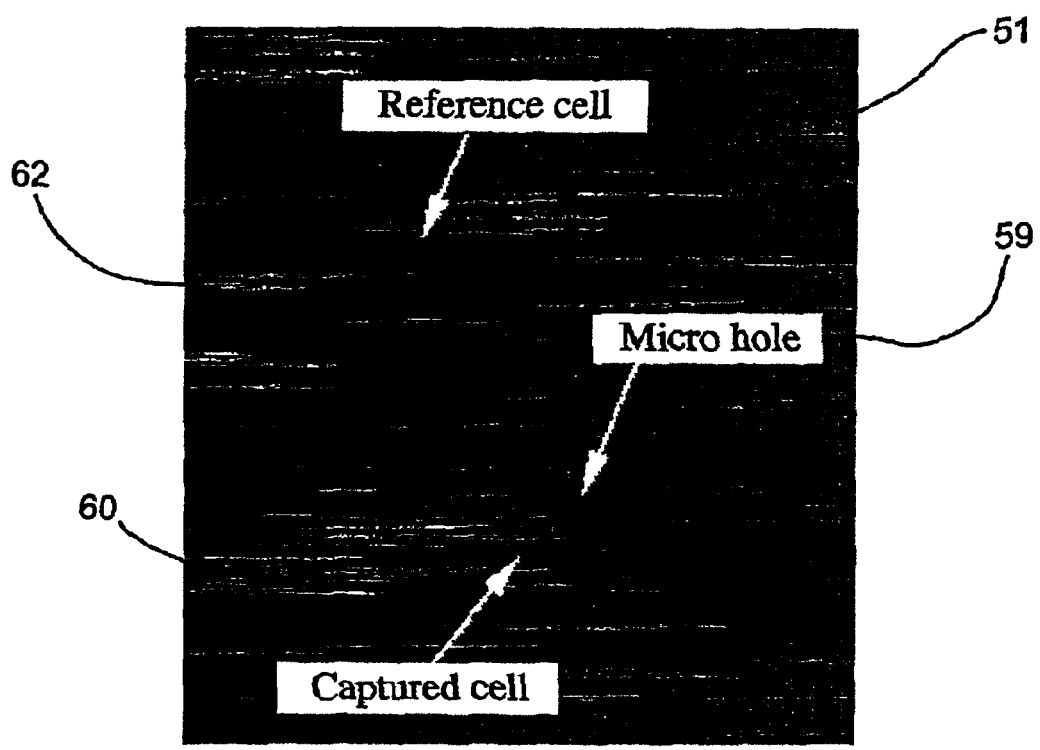
FIG. 13 is an actual photograph of cells being assayed in a device of the invention.

Referring to FIG. 13 it can be seen that the cell 60 can be viewed through the transparent electrode 51. Further, the microhole 59 can be viewed. The viewing is, of course, carried out by positioning a microscope over the transparent electrode 51. A fluorescent dye was used to demonstrate that the dye could be transported into the cell using a device of the invention.

Figure 14:
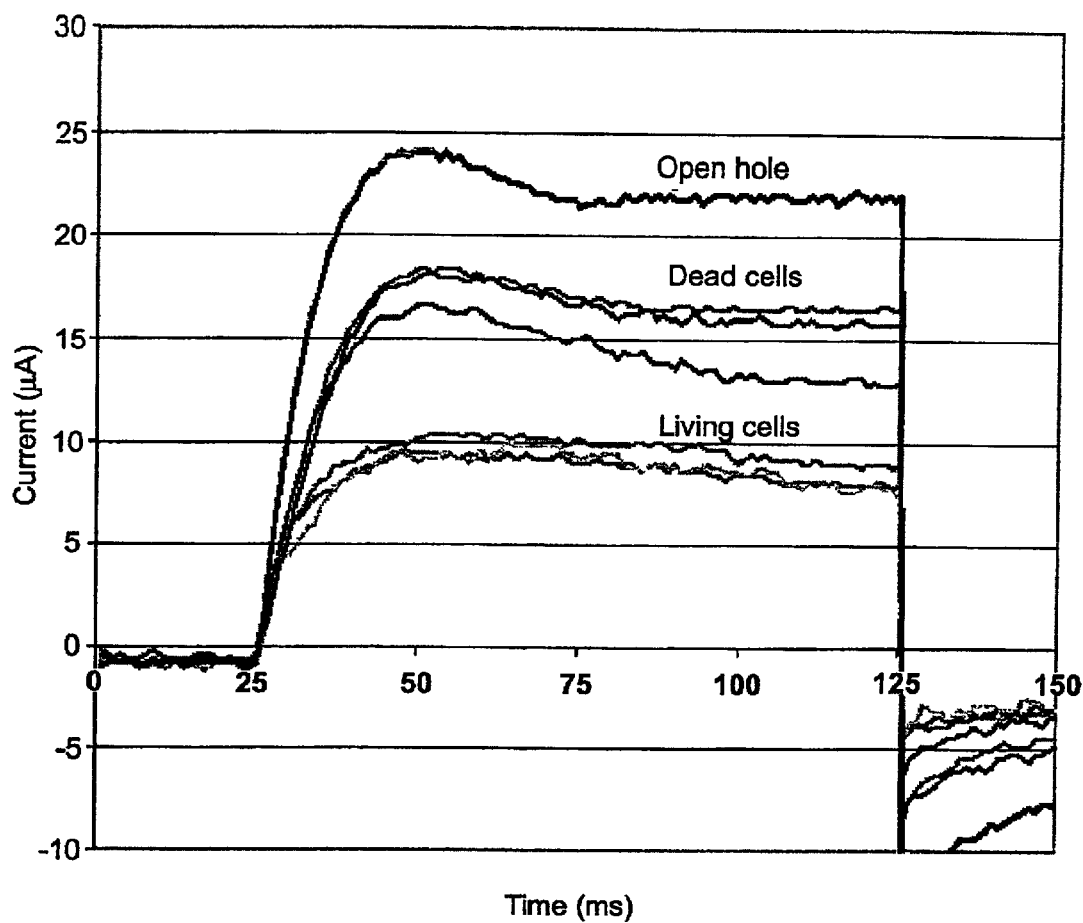
FIG. 14 is a graph of current versus time for assayed living cells, dead cells and the device without a cell present.

FIG. 14 is a graph showing current versus time for experiments carried out on the electrical response of a DU-145 cells placed within a device having a three micron hole 59 in the dielectric membrane 57 shown in FIG. 12. As shown in the graph of FIG. 14 some of the cells were diagnosed as being living cells whereas others having a higher current flow were clearly differentiated as being dead cells. The electrical response of the cells in the population which had taken up a dye referred to as YOYO-1 dye were compared with cells in the same population that did not take up the dye and therefore were not fluorescent. Taking up the dye implies that the cell membrane was impaired and therefore the cell was dead. The comparison showed a correspondence between the dead cells with high current detected and cells with the fluorescent dye.

Figure 15:
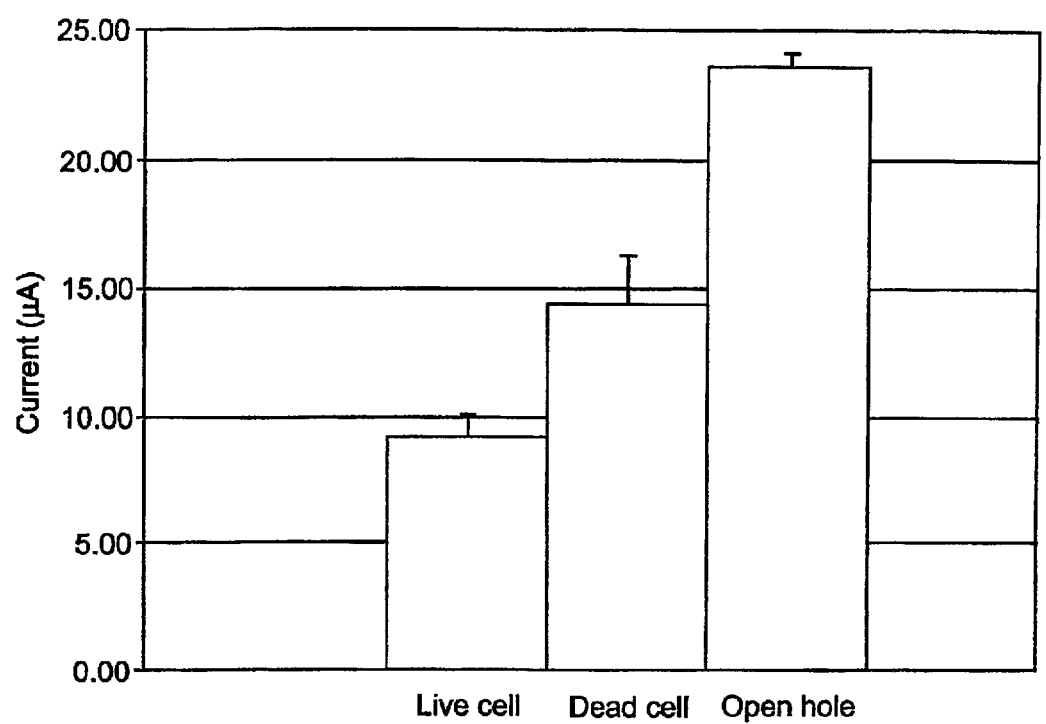
FIG. 15 is a bar graph representative of data shown in FIG. 14.

FIG. 15 shows bar graphs of the data of FIG. 14 where 10 volts is applied for 125 ms or less of electrical pulse. This pulse had previously been shown to induce reversible electroporation of the cell membrane in DU-145 cells. FIG. 14 shows the data comparatively for currents flowing through three fluorescing cells, three intact cells and the open-hole measurement. The results show that the electrical current through cells that were intact is substantially smaller than the electrical current through cells for which the uptake of the YOYO-1 dye indicates impaired membranes. Thus, FIG. 14 indicates a quantitative measure of the electrical response of membrane-impaired cells and membrane-intact cells. The results compare the average current at the end of an applied pulse for dead cells, living cells and the open hole. The electrical currents at the end of 10 volts applied for 100 ms through the intact cells (n=32) was 9.19±0.19 microamps. When the same pulse was applied to cells that fluoresce (n=22) the current was 14.39±1.9 microamps. This is a significant difference from the currents through the intact cells ($p<0.0001$).

These results show that the difference in electrical currents are a useful indication for distinguishing dead cells with impaired membranes from live cells with intact membranes. Unlike biochemical or biological assays this method provides instantaneous viability determinations because the electrical current measurement is instantaneous. The results shown in FIG. 14 in the graph are made into a bar graph in FIG. 15. It should be noted that there was considerable difference between the average content of naturally dead cells and the open-hole current (23.64±0.58 microamps). The electrical current ratio between dead cells and the open hole mode is 0.61. These results show that the damaged membrane of cells in a population that died from natural causes maintained integrity to a certain extent. Accordingly, there is still some resistance to ionic flow through the membrane of the dead cells.

Figure 16:
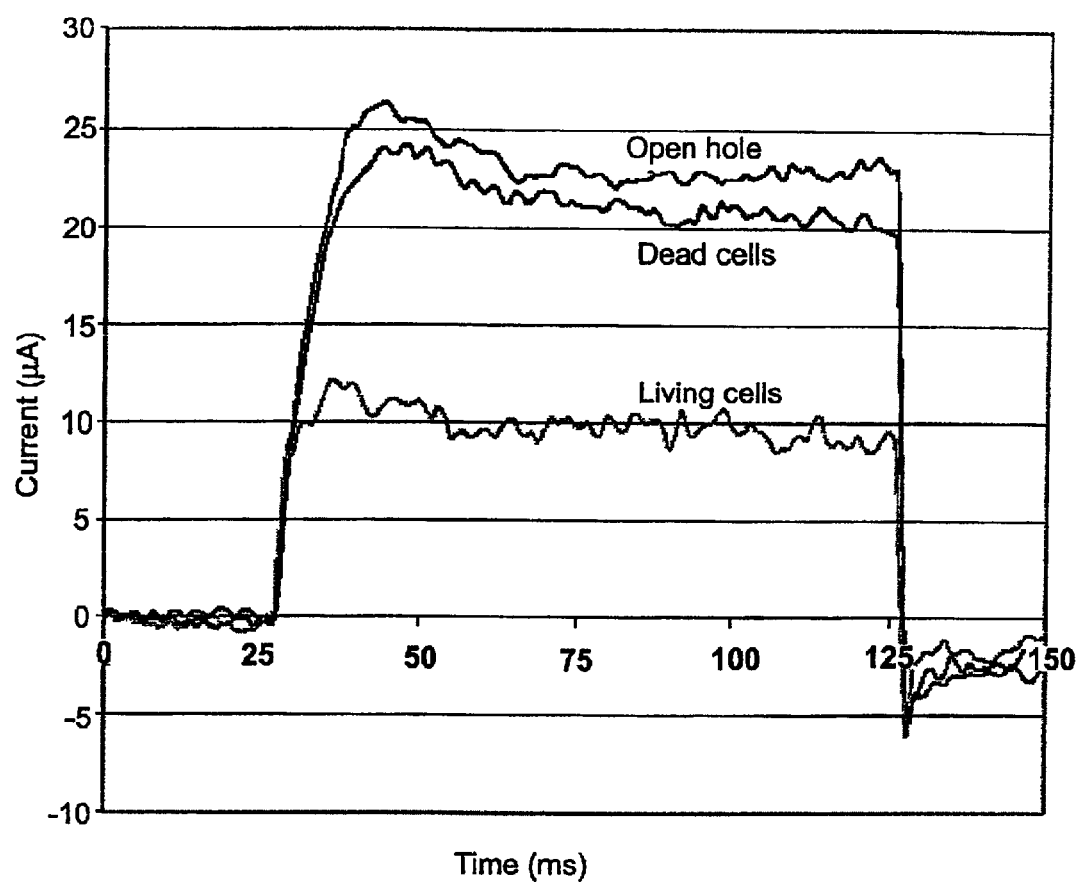
FIG. 16 is a graph of current versus time for living cells, dead cells and the device without a cell present.
Figure 17:
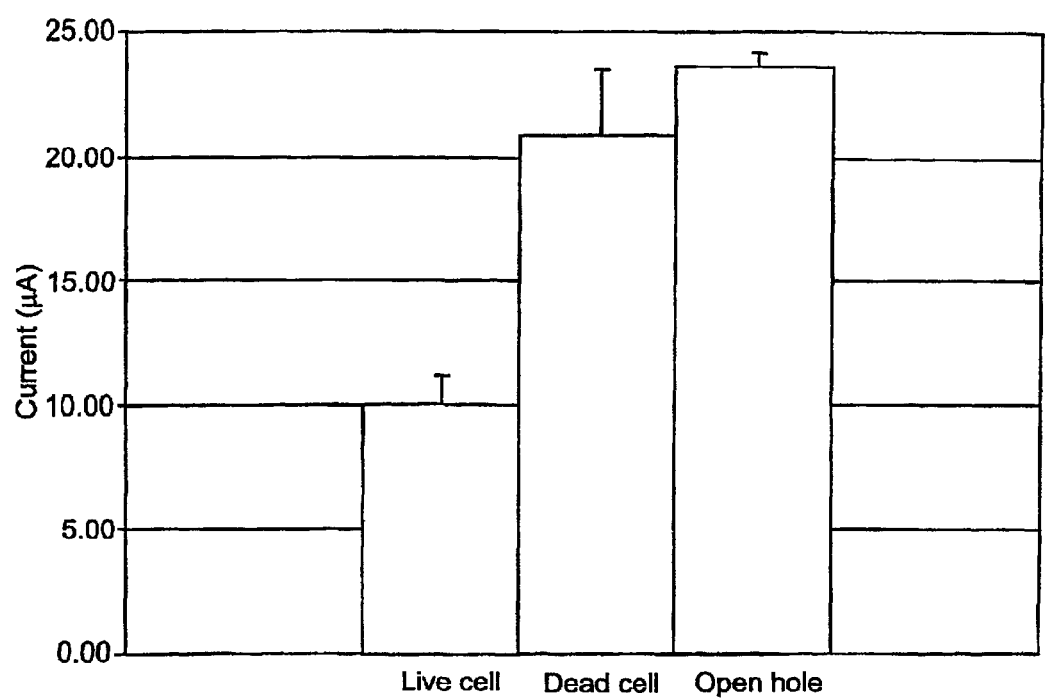
FIG. 17 is a bar graph representation of the data shown in FIG. 16.

The results of FIG. 16 are similar to those of FIG. 14. However, the results of FIG. 16 are those of experiments performed with the same three micrometer hole in the micro-electromechanical chip with ND-1 cells. The experimental results in these experiments compared the current through living cells with those through cells which were intentionally killed by inducing irreversible membrane electroporation in the cell membrane. Irreversible electroporation was obtained by continuously applying low amplitude electrical impulses until the cell fluoresced brightly under a fluorescent microscope. FIG. 16 shows that the chip currents for a fluorescing cell, intact live cell and open hole during the application of an electrical pulse of 10 volts per 100 ms. The pulse has been previously proven to induce reversible electroporation of the cell membrane in MD-1 cells. It is clear that the same electrical pulse produces a very different current through live and different cells. FIG. 16 compares the average current value at the end of the 10 volt 100 ms pulse for intact live cells (n=40) and irreversibly electroporated ND-1 cells (n=22). The significant difference ($p<0.0001$) in currents, 10.02±1.22 microamps v. 20.95±2.75 microamps, proves again that with the micro-electromechanical chip electrical current could be used as a direct and substantially instant test for viability. The data shows that currents through live ND-1 and DU-145 cells are statistically the same. The results obtained and shown in FIG. 16 are shown in a bar graph in FIG. 17. It should be noticed that the average chip currents for the irreversibly electroporated ND-1 cells was very close to the open hole current (20.95 microamps v. 23.64 microamps) and significantly larger than the current through the natural dead DU-145 cells (20.95 microamps v. 14.39 microamps). These results indicate that the magnitude of current through the cells should be related to the type of damage the cell membrane experiences. The higher current for ND-1 cells that experienced irreversible electroporation may imply that the extent of membrane damage due to irreversible membrane break down is greater than that due to natural lysis in DU-145 cells.

The results shown in FIGS. 14–17 clearly indicate that for the same electrical pulse the current through dead (membrane impaired) cells and live cells is detectable different. This indicates that measuring electrical current through cells is useful in determining cell membrane integrity and thereby deducing cell viability. This determination is comparable in accuracy to viability assays that use dyes to examine the integrity of cell membranes. However, the electrical current measurement is instantaneous and does not require the addition of chemical additives. In contrast, calorimetric and fluorescent measurements require the addition of chemicals and are not instantaneous. Furthermore, calorimetric or fluorescent dyes do not produce quantitative information on the magnitude of damage to the impaired cell membrane. The methodology of the present invention can be used to distinguish not only between dead and living cells, but between healthy living cells and living cells with impaired cell membranes.

By comparing the response of ND-1 cells whose membrane was damaged by irreversible electroporation with the response of naturally damaged DU-145 cells, it is shown that the mechanisms and magnitude of cell damage may also be distinguishable through quantitative analysis of the electrical current responses.

FIG. 12 shows that the device can be configured with a flow-through feature 63. Using this feature the device can be used to study the viability of individuals cells in a large population. Further, the device can be used to separate live cells from dead cells or separate live healthy cells with live healthy cell membranes from live cells with damaged cell membranes. The device could also be used to expose cells to various conditions including chemicals, pH changes, temperature and pressure changes. The changes in condition could be correlated against current flow in order to determine how these changes and conditions affect the cell membrane and thus affect the viability of the cell. These results can be further extrapolated on in order to determine additional information specific to certain cells including the cellular mechanisms involved in cell death. Thus, the assay methodology and device of the invention can be used not only to determine which cells are alive and dead but determine which surrounding environmental conditions are safe for particular types of cells.

The following experimental protocal was used in carrying out the experiments which resulted in the data shown in the FIGS. 14–17.

Experimental Protocol

Micro-electroporation chip: The design and operation of the micro-electromechanical chip used in this study has been described in several publications [Huang et al., *Biomedical Microdevices*, 18:368–375 (2000); Huang et al., *Sensor and Actuators*, A89:242–249 (2001)]. It combines the ability to focus electrical current through a cell, measure the electrical currents through the cell and observe the cell under a microscope. The cells can be examined in a flow-through configuration or individual cells can be maintained in the path of the current for continuous examination.

Cell Line: Human prostate adenocarcinoma cells (ND-1 cells line) [Narayan, P. and R. Dahiya, *Establishment of a human primary prostatic adenocarcinoma cell line* (ND-1). J. Urol., 1992, 148: 1600–1604] and human prostate carcinoma cells (DU145 cell line) [Stone et al., *Int. J. Cancer*, 21:274–281 (1978)] were used in the viability tests. Both cell lines were courtesy of San Francisco VA hospital (San Francisco, Calif.). All cell lines were maintained at 37° C. under a humidififed atomosphere at 5% $CO_2$ and 95% air in 75 $cm^2$ tissue culture flasks (Corning). The culture medium used for both cell lines is RPMI-1640 (Gibco, Grand Island, N.Y.) supplemented with 10% (v/v) fetal calf serum, 20 mM HEPES, penicillin (100 units/ml), streptomycin (100 m g/ml) and 1% (v/v) L-glutamine. For each experiment, cells from the confluent monolayer were removed by trypsinisation (trypsin 0.05%, EDTA 0.025%) (Gibco Grand Island, N.Y.) and re-suspended in Dulbecco's PBS (Sigma chemicals, St. Louis, Mo.) for use.

Dead Cell Stain: In order to correlate transmembrane current signals with cell viability, YOYO-1 (Molecular Probes, OR) was used to distinguish between dead and living cells. YOYO-1 is a membrane impermeant fluorescent nucleic acid stain that binds to DNA/RNA/ When under UV light excitation, the dye and nucleic acid complex emits strong green light. Because healthy cell membranes prevent YOYO-1 molecules from entering cells, the dye molecule will not stain living cells. In contrast, because dead cells loose membrane integrity, YOYO-1 dyes can enter those cells and cause them to fluoresce green under UV lights. Therefore, dead and living cells can be distinguished by examining their fluorescence under the microscope, i.e. dead cells are green fluorescent and living cells are dark. Typical YOYO-1 concentration used in our experiments was 1 $\mu$l/ml. The excitation and emission spectra of YOYO-1 are 491 nm and 509 nm respectively.

Experimental Procedure: Cells are transferred and suspended in DPBS solution with the YOYO-1 dye. The cell suspension is then injected in the top chamber of a micro-electroporation chip. Visually assisted by a microscope (BX60, Olympus), a cell is pulled toward the micro hole of the chip and then captured in the hole by applying a proper pressure difference between the top and bottom chamber of the chip. After the cell is captured, it is excited by UV light through a 488 nm filter to check whether it is a living or a dead cell. Then an electrical pulse, which does not damage the cell through irreversible membrane breakdown, is applied between the two electrodes of the chip. The corresponding current across the cell membrane is recorded with a Tektronix TDS220 digital oscilloscope and transferred to a computer for later analysis.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

A series of experiments was performed using a micro-electroporation system consisting of the microelectroporation device described above and shown in FIG. 2, combined with flow and pressure control units and pressure gauges for the liquids to be circulated through the upper and lower chambers, a variable DC power supply, a pulse generator and power amplifier for imposing voltage pulses across the device, a digital oscilloscope for monitoring the pulses, a fluorescent microscope, a CCD (charge coupled device) camera, and a computer with image processing and waveform processing software. Both chambers of the device were filled with physiological saline and cells were introduced into the upper chamber. Liquid motion in the top and bottom chambers was controlled by syringes. The pressure in the upper chamber was atmospheric while the pressure in the lower chamber was reduced below atmospheric by pulling on the barrel of the syringe connected to that chamber. The voltage was applied in single square pulses ranging from zero to 120V in magnitude and from 2 microseconds to 100 milliseconds in duration. The distance between the electrodes in the upper and lower chambers was 900 microns.

The tests in this example were performed using ND-1 human prostate adenocarcinoma cells with a typical diameter of 20 microns. The opening in the microelectroporation device was 5 microns in diameter. A rectangular voltage pulse was applied with a duration of 60 milliseconds, and the pulse was applied at various amplitudes ranging from 10V to 60V in increments of 5 volts. With each pulse, the electric current passing through the opening was measured. Experiments were performed with the cells and were repeated both with the opening stopped by a glass bead and with no obstruction at all in the opening. The results in each case were expressed as microamperes of current vs. volts of pulse amplitude and are plotted in FIG. 4, in which the upper curve (data points represented by x's) represents the unobstructed opening, the lower curve (data points represented by asterisks) represents the data taken with the glass bead residing in the opening, and the three middle curves (open squares, open upright triangles, and open inverted triangles) represent data taken with three different ND-1 cells residing in the opening.

The upper curve shows that the current increases in a substantially steady manner as the voltage increases when there is no barrier to the passage of current through the opening. The lower curve also shows a substantially steady rise as the voltage increases, although at a much lower level. The current values shown in the lower curve represent stray currents through the device. The curves of data taken with the ND-1 cells across the opening show that at low voltages the current is close in value to that obtained when the opening is closed by the glass bead while at high voltages the current rises to the levels obtained with an unobstructed opening. The transition is a sharp increase which is indicative of the formation of pores in the cell membrane through which an electric current can pass, i.e., the onset of electroporation. In all three cells, the transition occurred at voltages between 30V and 40V. In two of the three cells (open squares and open upright triangles), the onset of electroporation occurred essentially at the same voltage, while in the third (inverted triangles), the onset occurred at a voltage that was lower than the other two by about 5V. This illustrates the value of controlling the process for individual cells to achieve optimal results.

Figure 4:
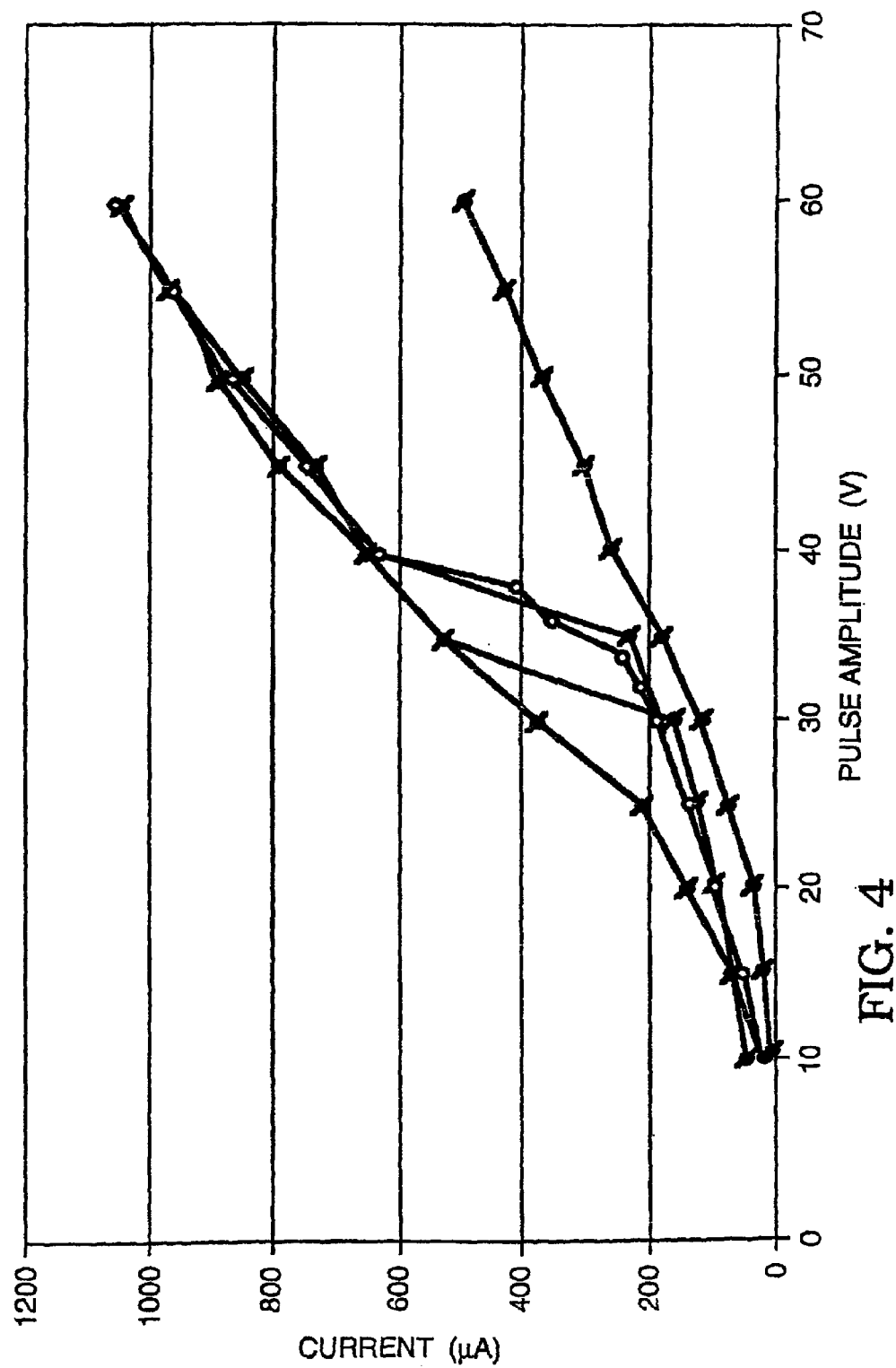
FIG. 4 is a plot of current vs. voltage in a series of electroporation experiments conducted using a microelectroporation device of the structure similar to that of FIG. 2.

After the data shown in FIG. 4 was generated, the pulses were reapplied in descending order of amplitude values, and the resulting curves displayed hysteresis, i.e., the curves obtained with descending amplitudes were higher in voltage than those obtained with ascending amplitudes. This indicated that the electroporation in these experiments was irreversible.

Example 2

Using the same microelectroporation system used in Example 1, a series of tests were performed on rat hepatocytes (ATCC #CRL-1439), whose typical cell diameter was 20 microns, the microelectroporation apparatus having an opening that was 4 microns in diameter. Here as well, rectangular voltage pulses that were 60 milliseconds in duration were used, ranging in amplitude from 10V to 37.5V in increments of 5 V in the portion from 10V to 30V and in increments of 2.5V in the portion from 30V to 37.5V. The experiments were performed in some cases only by increasing the amplitudes and in others by first increasing, then decreasing the amplitudes to evaluate reversibility. The results are plotted in the graphs shown in FIGS. 5a, 5b, 5c, and 5d. In each case, the upper curve (data points represented by circles) is the data taken with neither a cell nor a glass bead residing in the opening, the lower curve (data points represented by squares) is the data taken with a glass bead in the opening, and the middle curve (data points represented by triangles) is the data taken with a hepatocyte in the opening, using different hepatocytes for each of the four Figures.

Figure 5B:
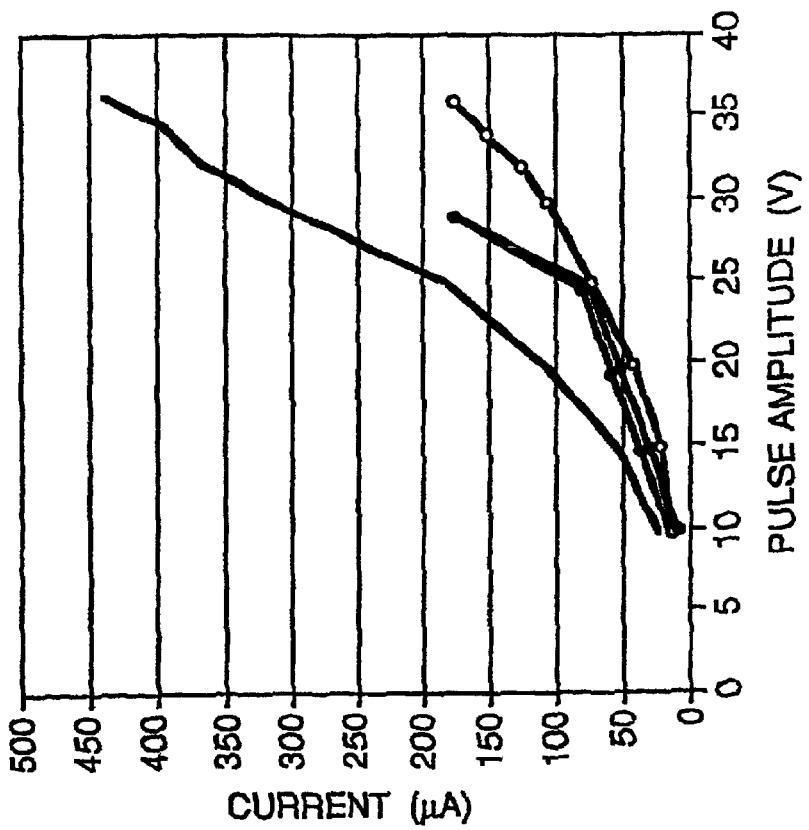
FIGS. 5a, 5b, 5c, and 5d are plots of current vs. voltage in a further series of electroporation experiments conducted using a microelectroporation device similar to that of FIG. 2.
Figure 5A:
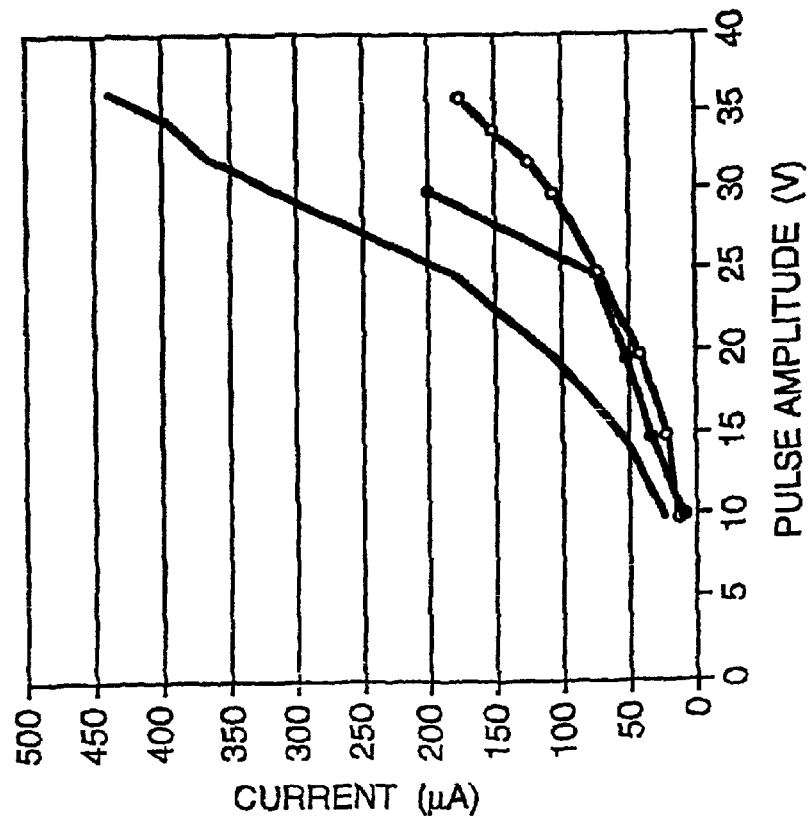
Figure 5D:
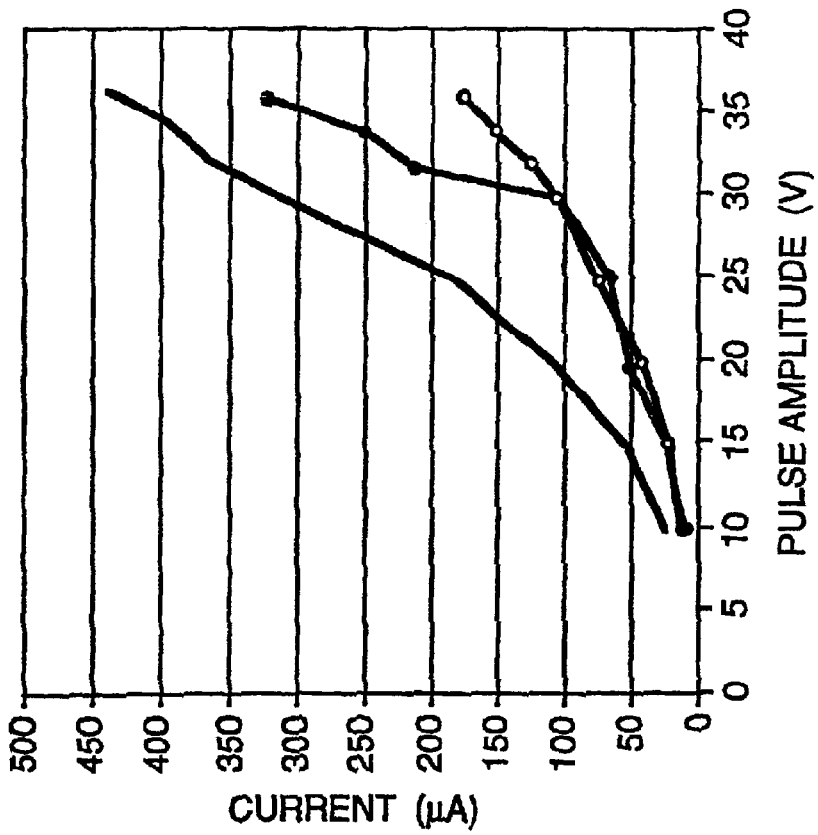
Figure 5C:
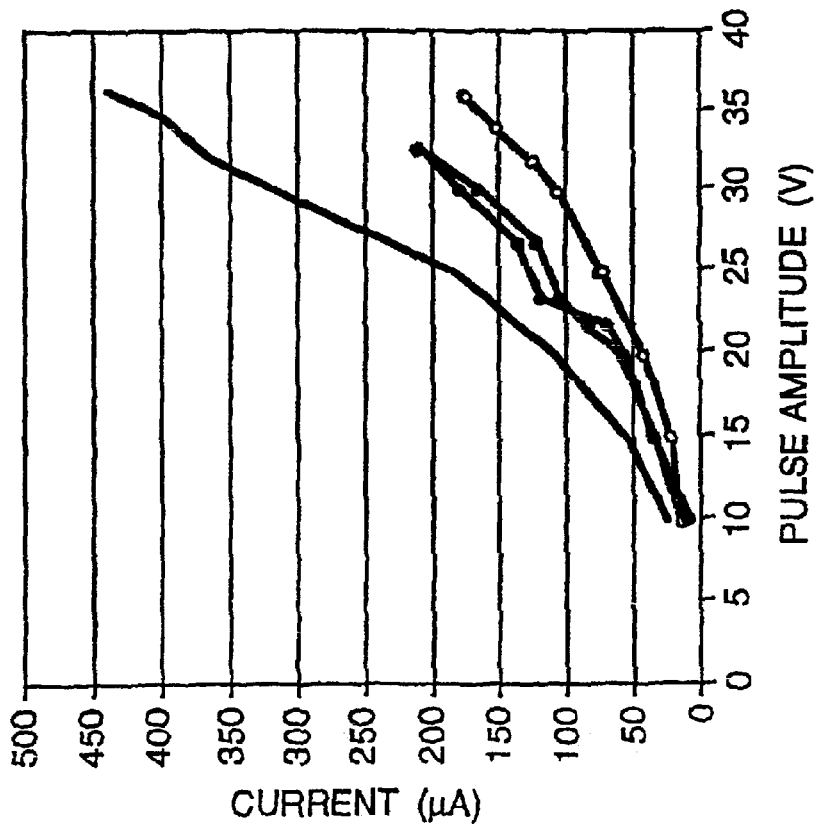

In FIG. 5a, the amplitude was increased and not decreased, displaying an electroporation threshold voltage of between 25V and 30V. In FIGS. 5b and 5c, the amplitude was first increased and then decreased to produce the two middle curves. Although the ascending and descending curves are not differentiated, they are substantially identical in each Figure, indicating that the cell membrane in each of these two cases resealed after each voltage pulse and thus that the pore formation was reversible. In the test represented by FIG. 5d, the cell disintegrated once the applied voltage exceeded 37.5V, although this is not shown in the Figure. It is significant to note that despite the fact that the same cell types were used in each of FIGS. 5a, 5b, 5c, and 5d, the electroporation threshold voltage differed among the individual cells, although all were within the range of 20V to 35V. Adaptation of the procedure to individual cells is readily achieved by monitoring the current in this manner to note when the electroporation threshold occurs. Selection of the optimal exposure time, voltage, composition changes in the surrounding liquids, and other parameters of the system can then be made to achieve the desired treatment of the cell without destruction of the cell.

The methods described herein are useful tools in the laboratory for conducting fundamental research in the electroporation properties of biological cells, and useful tools in industry for processing large quantities of cells in a flow-through manner. By enabling one to observe and record the current flowing through individual cells, one can control the amplitude and duration of the voltage pulse to achieve optimal results. In addition, the devices described and shown herein for use in practicing the invention can be constructed with transparent parts and of a size suitable for mounting on a microscope stage. This will permit one to correlate the electrical current measurements to visual observations and fluorescence measurements inside the cell. The device can be used to electrically detect, through the measurement of currents, the point in time when a cell becomes lodged in the opening as well as the point in time when pore formation is achieved in the cell membrane. For larger scale and industrial applications, large numbers of microelectroporation devices of the type described herein can be arranged in parallel. For each cell, electrical information indicating the trapping of a cell in the opening (such as a sharp drop in the current) can be used to generate a signal that will initiate an electroporation sequence, and further electrical information indicating the completion of electroporation (such as a sharp rise in current) will generate a signal that will release the cell (for example by eliminating or reversing the pressure differential) and permit the next cell to flow toward the opening.

In addition to using the device and system of the invention to move a material into or out of the cell the system and device can be used in a diagnostic or analytic mode. This is carried out by measuring electrical impedance of a cell or cells placed in a medium and using the measured electrical impedance information. It is possible to deduce information relating to the integrity of cell membranes and thus provide for analysis. It is also possible to compare the information to information previously obtained on normal or diseased cells of the same type and thereby obtain diagnostic information. For example, the electrical impedance of a cell with an intact membrane will be much high than the impedance of the same cell with impaired membrane. Thus, analytically the process can provide information with respect to the structural integrity of the cell membrane. Diagnostically the method can provide information with respect to the relative structural integrity of cell membranes.

Example 3

Electrical Impedance Mapping of Electroporated Domains

In order to illustrate the ability of EIT to monitor electroporation in tissue we have solved a mathematical simulation of the problem.

Figure 9:
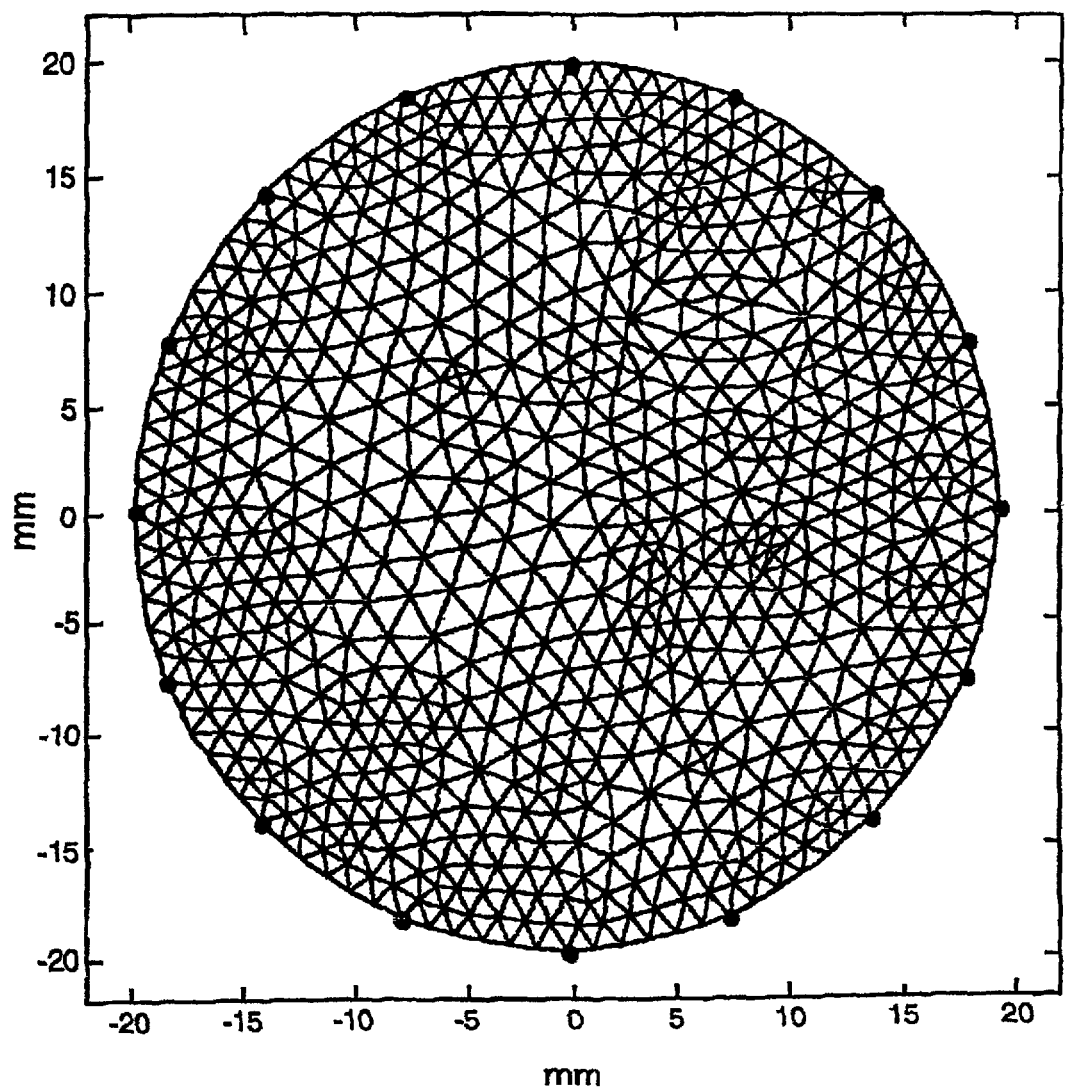
FIG. 9 is a graphic schematic view of a finite element mesh showing a circular region of tissue bounded by electrodes (dark dots)—the domain has two different impedances.
Figure 10:
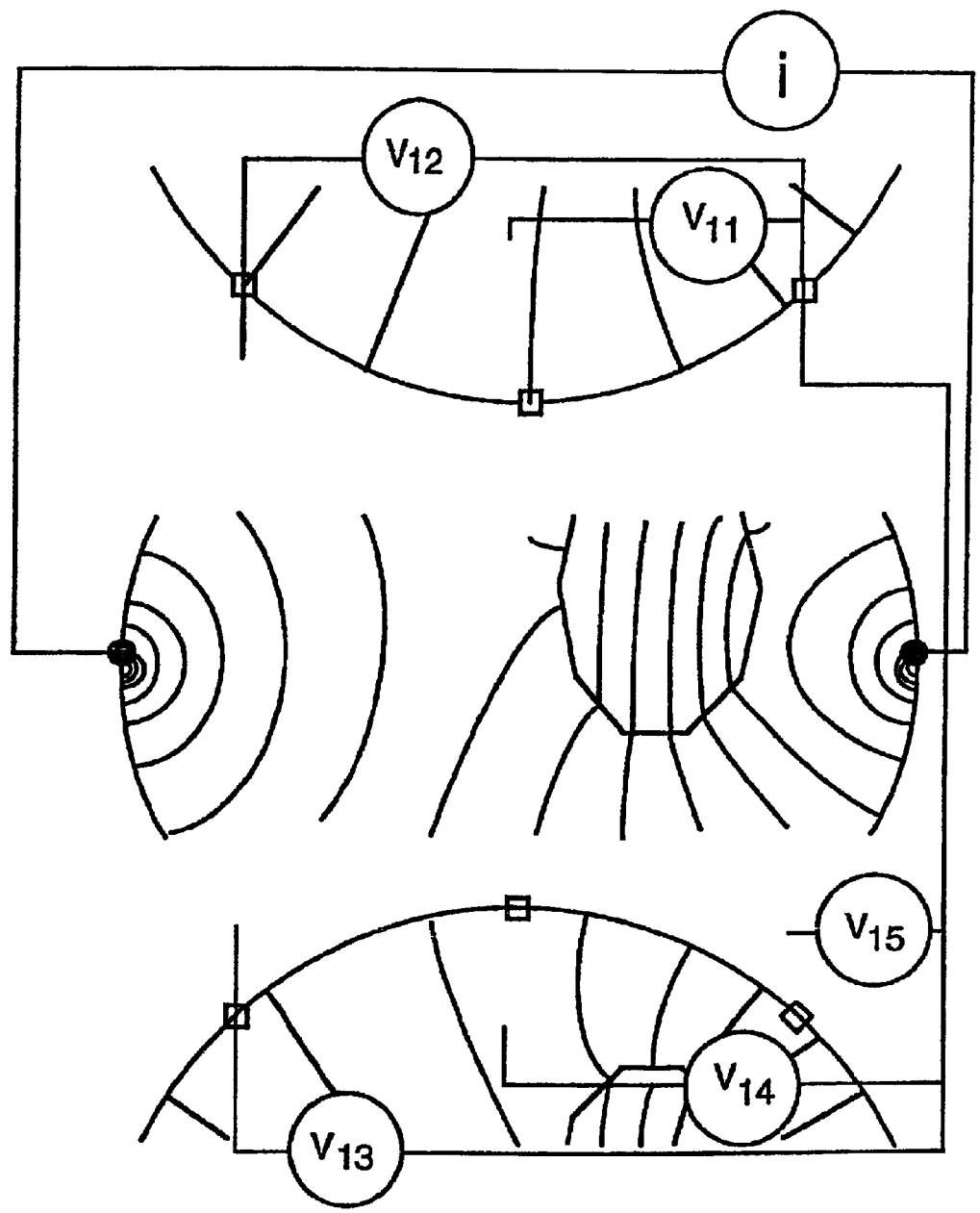
FIG. 10 schematically shows typical electrode configuration, measured electrical variables and equipotential lines in a circular domain having an inclusion with a different electrical impedance.

To provide the necessary data for electroporation imaging simulation, a simulated tissue phantom was created first using a 2-D fine-mesh FEM model (~1600 nodes, ~3100 elements). The phantom, shown in FIG. 9, consisted of a circular imaging domain (20 mm radius, resistivity 500 ohm cm for muscle with a variable number of point source electrodes equally spaced around the periphery. Within this imaging region, a single arbitrarily shaped electroporated region was defined with a different resistivity. An opposite electrode current injection pattern was used, providing $N(N-1)/2$ independent voltage measurements where N is the number of electrodes. The model was solved using the adaptive mesh generation and FEM solution algorithms available in MATLAB's Partial Differential Equation Toolbox (The Mathworks Inc.). An example mesh for the given geometry is shown in FIG. 9. The information that the phantom module makes available to the reconstruction algorithms represents data that would have been available during the electroporation part of an experiment, i.e current and voltage at the different electrodes around the tissue. From this data we attempted to reconstruct the original image of the tissue that was input in the model. (It should be noted that a DC injection current was used in place of the AC current typical to EIT in order to simplify the problem. The AC derivation and implementation is a straightforward extension of that presented here.) A typical example for the voltage and current distribution in the phantom during a simulated data acquisition step for an 8-electrode EIT system is illustrated in FIG. 10.

Figure 11:
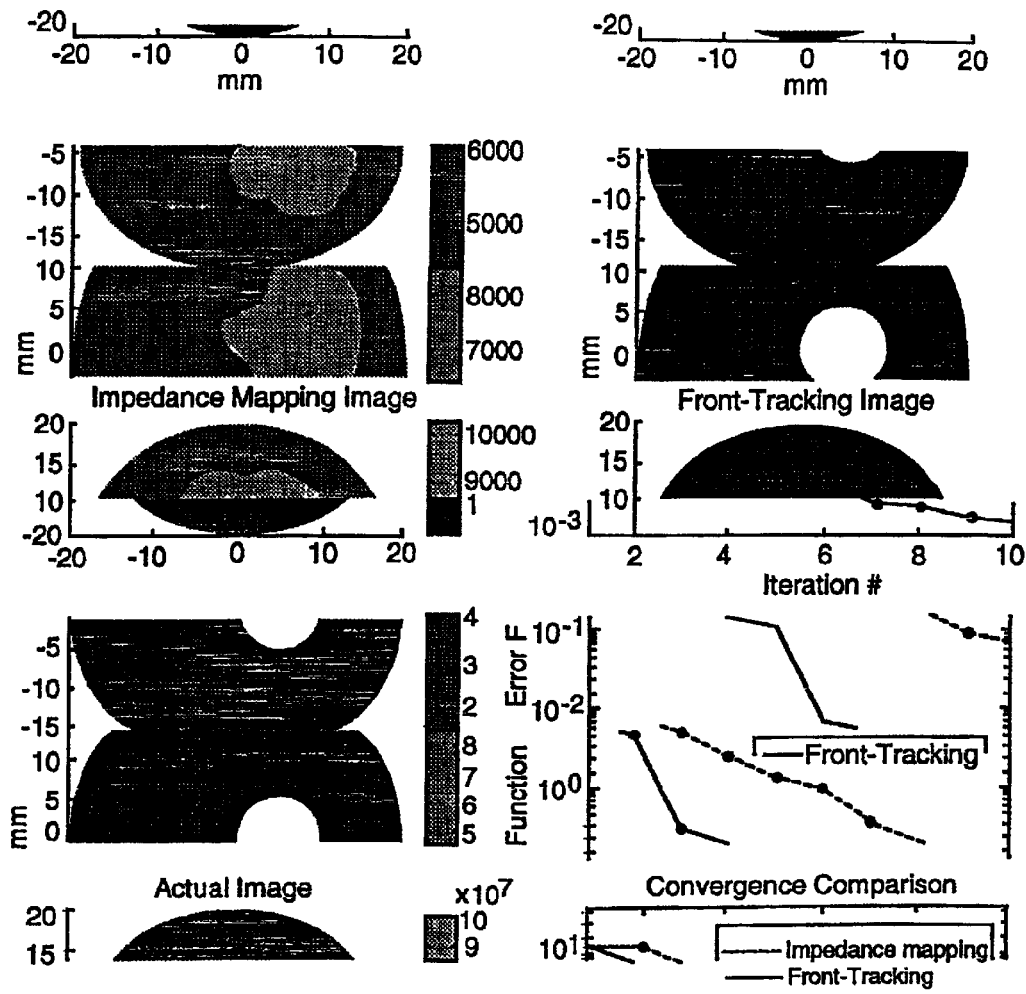
FIG. 11 shows an actual image in the top left whereas the impedance mapping is shown in the bottom right which shows differential impedance mapping.

The data obtained from the phantom was input into two EIT imaging algorithms, one using the finite element method and the second the boundary element method to generate the impedance image. The algorithms use a standard Newton Raphson technique to produce the image. FIG. 11 compares the image of a circular domain with two different electrical impedances in comparison to the image of the original phantom as recreated with the finite element technique and with the boundary element technique.

Electrical impedance tomography can be used to image the electroporated region in tissue because EIT produces an image of the tissue from a map of the electrical impedance of the tissue and electroporation produces changes in impedance. The electrodes for tissue electroporation imaging may be different than those used for the electroporation process itself or may be the same.

Example 4

Electrical Detection of Change in Membrane Permeability

As part of our research on cell electroporation we have studied the electrical characteristics of cells during reversible and irreversible electroporation. In reversible electroporation the cell is not damaged by the electroporation process and the membrane reseals. In irreversible electroporation the cell membrane is damaged and does not reseal. In a set of experiments in which we have used ND-1 cells to measure currents through cells in the micro-electroporation chip we have obtained results illustrated by FIGS. 8a and 8b. The results were obtained by exposing cells to triangular shaped electrical pulses (top curve) in 8a and 8b. The electrical currents flowing through the cells are shown in the bottom curve in 8a and 8b. FIG. 8a is for a cell that was irreversible electroporated and FIG. 8b for a cell that was reversible electroporated. It can be easily noted that when the voltage was reduced in the reversible electroporated cell it retained the same values as during the voltage increase stage. However, in the irreversible case the current through the cell with the damaged membrane had a higher current than in the intact cell. This leads to the conclusion that electrical currents flowing through cells can provide indication on changes in membrane permeability in general and a measure of the integrity of the cell membrane in particular under a variety of situations and not only during electroporation. For instance, cell viability is often measured with trypan blue or fluorescence dyes that penetrate through damaged membranes. These results show that an alternative method for detecting cells with damaged membranes would be to measure the electrical current-voltage relation across the cell. Similarly, there are compounds that induce pores in the cell membrane, such as ionophors. Measuring the current-voltage (impedance relation across a cell membrane could also detect if the membrane was impaired by these chemicals). Electrical measurements would have advantage over chemical means for detecting cell membrane damage because they would produce immediate information. A possible method for detecting changes in cell membrane permeability and in particular damaged cell membranes is to use the electroporation chip as described for the process of electroporation. The measure of damage would be the difference between an intact cell impedance and a damaged cell impedance as illustrated in FIGS. 8a and 8b. In tissue it would be possible to detect cells with damaged membranes in a similar way to the methods for detection of electroporation described here.

Example 5

Electrical Impedance Mapping if Non-Viable Areas of a Tissue

In order to illustrate the ability of EIT to monitor the viability of cells and non-viable cells in tissue we have solved a mathematical simulation of the problem.

To provide the necessary data for non-viable tissue imaging simulation, a simulated tissue phantom can be created first using a 2-D fine-mesh FEM model (~1600 nodes, ~3100 elements). The phantom, shown in FIG. 9, consisted of a circular imaging domain (20 mm radius, resistivity 500 ohm cm for muscle with a variable number of point source electrodes equally spaced around the periphery. Within this imaging region, a single arbitrarily shaped non-viable tissue region can be defined with a different resistivity. An opposite electrode current injection pattern can be used, providing N(N−1)/2 independent voltage measurements where N is the number of electrodes. The model may be solved using the adaptive mesh generation and FEM solution algorithms available in MATLAB's Partial Differential Equation Toolbox (The Mathworks Inc.). An example mesh for the given geometry is shown in FIG. 9. The information that the phantom module makes available to the reconstruction algorithms represents data that would have been available during the EIT reconstruction part of an experiment, i.e current and voltage at the different electrodes around the tissue. From this data one can reconstruct the original image of the tissue that was input in the model. (It should be noted that a DC injection current may be used in place of the AC current typical to EIT in order to simplify the problem. The AC derivation and implementation is a straightforward extension of that presented here.) A typical example for the voltage and current distribution in the phantom during a simulated data acquisition step for an 8-electrode EIT system is illustrated in FIG. 10.

The data obtained from the phantom can be input into two EIT imaging algorithms, one using the finite element method and the second the boundary element method to generate the impedance image. The algorithms use a standard Newton Raphson technique to produce the image. FIG. 11 compares the image of a circular domain with two different electrical impedances in comparison to the image of the original phantom as recreated with the finite element technique and with the boundary element technique.

Electrical impedance tomography can be used to image the non-viable region in tissue because EIT produces an image of the tissue from a map of the electrical impedance of the tissue and cell death produces changes in impedance.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of determining cell viability, comprising the steps of:
   (a) placing a first cell in an electrically conductive medium wherein said first cell blocks an opening in a material which material blocks current flow;
   (b) applying a voltage across said first cell;
   (c) detecting electrical current through said first cell;
   (d) comparing the detected electrical current across said first cell to a standard comprising a previous reading on a second cell that has a known viability in order to determine the viability said first cell.

2. The method of claim 1, further comprising:
   (e) repeating steps (a)–(d) a plurality of times with a different first cell each time.

3. The method of claim 1, wherein said first cell is held in a opening in a material which blocks current flow.

4. The method of claim 1, wherein a plurality of first cells are placed in the electrically conductive medium in the opening of the material which blocks current flow.

5. A method of determining cell viability, comprising the steps of:
   (a) placing a first cell in an electrically conductive medium wherein said first cell blocks an opening in a material which material blocks current flow and said first cell is held in an opening in the material;
   (b) applying a voltage across said first cell;
   (c) detecting electrical current through said first cell;
   (d) comparing the detected electrical current across said first cell to a standard comprising a previous reading on a second cell that has a known viability in order to determine the viability of said first cell; and
   (e) repeating steps (a)–(d) a plurality of times with a different first cell each time to determine viability of each first cell.

6. The method of claim 1, wherein the voltage applied across said first cell is a direct current (DC) pulse voltage.

7. The method of claim 5, wherein the voltage applied across said first cell is a direct current (DC) pulse voltage.

8. The method of claim 1, wherein the previous measurement is obtained from a second cell substantially identical to said first cell of steps (a)–(c).

9. The method of claim 8, wherein the second cell has been subjected to a condition affecting cell viability.

10. The method of claim 9, wherein the condition is temperature, pressure, pH, radiation or exposure to a substance.

11. The method of claim 10, wherein the condition is radiation selected from the group consisting of UV, visible and infrared.

12. The method of claim 1, wherein the second cell is a normal cell.

13. The method of claim 1, wherein the second cell is a diseased cell.

14. The method of claim 9, wherein the condition is exposure to a substance selected from the group consisting of a protein, a nucleotide sequence, a bacteria, a virus, an infectious prion, a fungus and a polysaccharide.

15. The method of claim 5, wherein the previous measurement is obtained from a second cell substantially identical to said first cell of steps (a)–(c).

16. The method of claim 15, wherein the second cell has been subjected to a condition affecting cell viability.

17. The method of claim 7, wherein the condition is temperature, pressure, pH, radiation or exposure to a substance.

18. The method of claim 17, wherein the condition is radiation selected from the group consisting of UV, visible and infrared.

19. The method of claim 16, wherein the condition is exposure to a substance selected from the group consisting of a protein, a nucleotide sequence, a bacteria, a virus, an infectious prion, a fungus and a polysaccharide.

* * * * *